(12) United States Patent
Riley et al.

(10) Patent No.: US 6,453,060 B1
(45) Date of Patent: Sep. 17, 2002

(54) METHOD AND APPARATUS FOR DERIVING SEPARATE IMAGES FROM MULTIPLE CHROMOGENS IN A BRANCHED IMAGE ANALYSIS SYSTEM

(75) Inventors: James K. Riley, Redmond; Michael G. Meyer, Seattle; David J. Perry, Woodinville; Andrew D. Silber, Kirkland, all of WA (US)

(73) Assignee: Tri Path Imaging, Inc., Burlington, NC (US)

(*) Notice: Subject to any disclaimer, the term of this patent is extended or adjusted under 35 U.S.C. 154(b) by 0 days.

(21) Appl. No.: 09/343,172

(22) Filed: Jun. 29, 1999

(51) Int. Cl.[7] ................................................. G06K 9/00
(52) U.S. Cl. ......................................... 382/133; 377/10
(58) Field of Search ............................... 382/133, 130, 382/134, 165, 171; 377/10

(56) References Cited

U.S. PATENT DOCUMENTS

| | | | | |
|---|---|---|---|---|
| 4,998,284 A | * | 3/1991 | Bacus et al. | 382/133 |
| 5,933,519 A | * | 8/1999 | Lee et al. | 382/133 |
| 6,134,354 A | * | 10/2000 | Lee et al. | 382/133 |
| 6,165,734 A | * | 12/2000 | Garini | 435/7.21 |
| 6,198,839 B1 | * | 3/2001 | Kuan | 382/133 |

FOREIGN PATENT DOCUMENTS

WO      9720198      6/1997

OTHER PUBLICATIONS

Chroma Vision, Product, Press Releases, Stock Information.
Hogan, Hank, "Imaging System Hunts the Human Haystack for Cancer Cells", *Biophotonics Internationa*, May/Jun. 1999, pp. 28–29.

* cited by examiner

*Primary Examiner*—Leo Boudreau
*Assistant Examiner*—Barry Choobin
(74) *Attorney, Agent, or Firm*—George A. Leone, Sr.; Hans I. Sun

(57) ABSTRACT

A system for collecting images at multiple wavelengths for image analysis of biological specimens. The process separates contrasts for images of a biological specimen prepared with a chromogen. Light wavelengths matched with each chromogen optimize separation for each image. Computing attenuation coefficients and extinction coefficients for each chromogen provides for determination of the concentration of each chromogen. A chromogen separator allows for subtracting predetermined chromogens to generate new images and aid in identification of cell morphology. The system can perform the image analysis of the new images using image processing techniques such as segmentation, feature calculation and object classification. At each stage of image processing, data from each of the new images may influence the processing of the other images.

15 Claims, 17 Drawing Sheets

System for Collecting Images at
Multiple Illumination Wavelengths

System for Collecting Images at
Multiple Illumination Wavelengths

Applying the Chromogen Separator

Offline Measurement of Extinction Coefficients

Image Collected Using 509 nm Filter

Image Collected Using 555 nm Filter

Image Collected Using 608 nm Filter

Mask for Selecting Nuclei

Image at 555 nm minus Chromogen 1

Both Chromogens Removed from Image
Collected Using 555 nm Filter

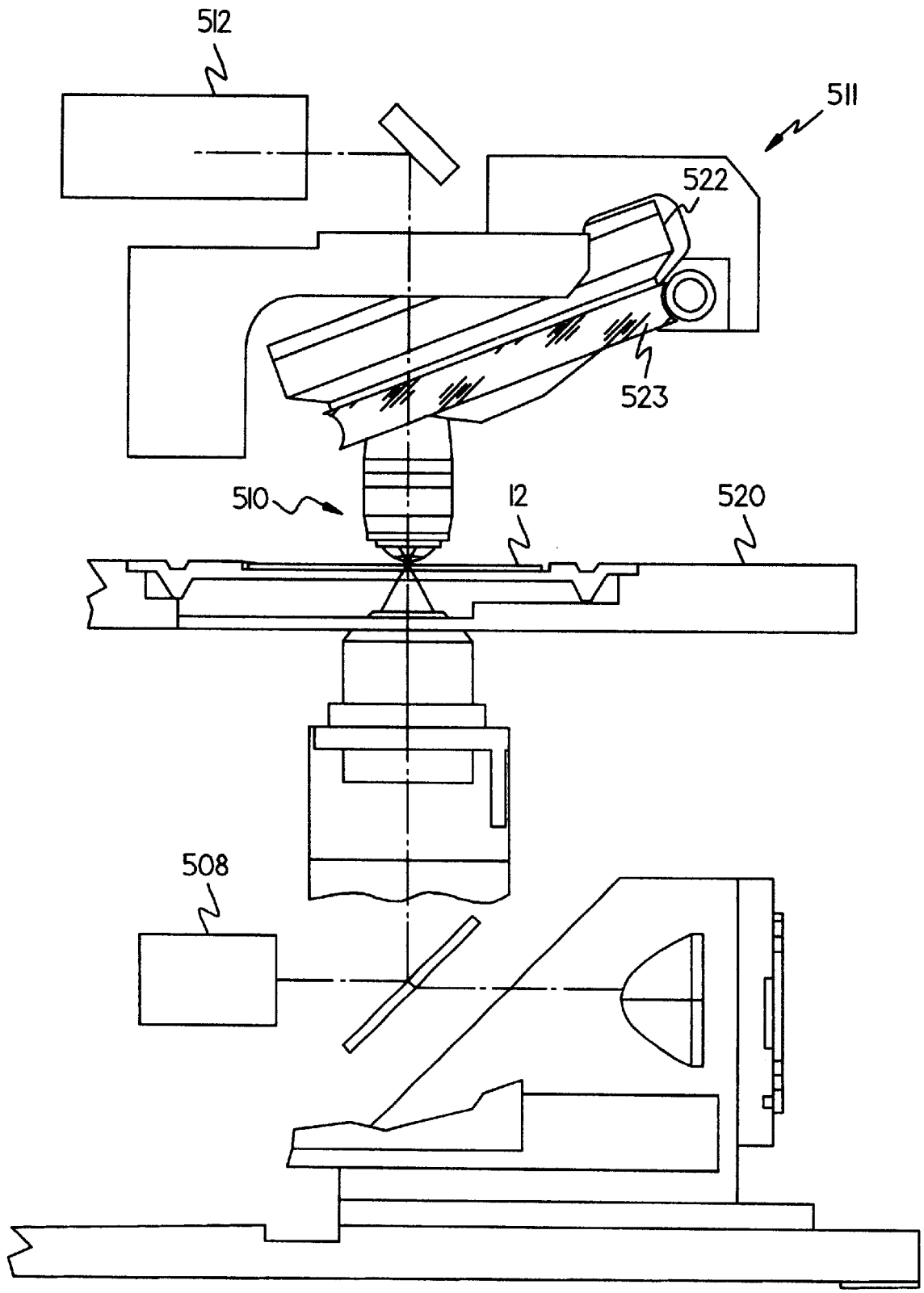
Fig_15C

METHOD AND APPARATUS FOR DERIVING SEPARATE IMAGES FROM MULTIPLE CHROMOGENS IN A BRANCHED IMAGE ANALYSIS SYSTEM

FIELD OF THE INVENTION

The invention relates to the use of molecular markers in an automated microscope utilizing computer image analysis for biological specimens.

BACKGROUND OF THE INVENTION

A molecular marker is a chemical that binds with high specificity to a predetermined chemical target inside or on the surface of a cell or to particular molecules suspended in a biological fluid specimen. In common use are molecular markers for proteins, in which case a marker acts as an antibody to a target antigen, and for nucleic acids, in which case a marker is a strand of DNA or RNA with a base sequence complementary to that of the target. Attachment of the antibody to the antigen is called "binding". Attachment of the nucleic acid probe to its complement is called "hybridization". Automated detection and localization of these attachments and, in some cases, quantification of the amount of target chemical attaching itself to targets, can improve the performance of automated microscopes used to screen specimens for indications of disease. These same methods can also be useful in research for medicine and biology, discovery and testing of pharmaceuticals and in toxicological testing of chemical agents.

The invention applies to molecular markers that utilize light absorbing dyes, also known as chromogens, as opposed to dyes that fluoresce in the presence of excitation or that radiate photons as a product of radioactive decay or chemical reaction. The general approach to staining a specimen with such a marker comprises the steps of concentration, capture, fixation, incubation, and development. Concentration and capture take many forms, but result in the attachment of the cells or molecular components of interest to some surface suitable for examination by the microscope. Fixation lyses the cells in the specimen and preserves them from decay. Incubation exposes the cells or biological fluid to the antibody or nucleic acid molecules, which have been attached to substrate molecules that accomplish the staining. Antigen-antibody binding or nucleic acid hybridization occur during incubation. During development, the substrate undergoes a reaction typically catalyzed by an enzyme to produce an insoluble, light-absorbing precipitate. A further step in the development process includes washing away the unbound marker, leaving precipitate only in those areas where binding or hybridization have occurred.

Chromogens are selected for their light absorption characteristics. Absorption of a particular wavelength produces color at a complementary wavelength. Multiple chromogens can be used on a specimen. Typically, a set of chromogens is used to stain cellular structures for morphological analysis and a single chromogen that yields a distinctive color is used as a molecular marker.

When such biochemical markers are used in conventional microscopy, a trained specialist views the image from the microscope and searches for structures of the color produced by the chromogen of interest. A judgement is then made of the clinical significance of the appearance, if any, of the marker. This judgement may be based on the identification of cell type and degree of morphological abnormality of the cells stained by the marker as well as the concentration of the marker stain.

Therefore, it is one motivation of the invention to provide an automated screening system that uses this information to automatically analyze a biological specimen. It is a further object of this invention to separate molecular marker information from morphological features.

SUMMARY OF THE INVENTION

A method for biological specimen image analysis on a plurality of images collected at multiple wavelengths comprising the steps of: applying a chromogen separator to the plurality of images to generate a set of new images; segmenting the each image of the set of new images to provide a plurality of segmented outputs; performing feature calculation on each of the plurality of segmented outputs wherein data from each of the segmented outputs is used on each feature calculation to provide a plurality of feature calculation results; performing object classification on each of the feature calculation results wherein data from each of the feature calculation results is used on each object classification to provide a plurality of object classification results; integrating the object classification results to provide a field of view score integrated output; and generating a slide score from the field of view score integrated output.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIGS. 15A, 15B and 15C show an apparatus for automated biological specimen analysis.

DETAILED DESCRIPTION OF THE PREFERRED EMBODIMENT

Figure 1:
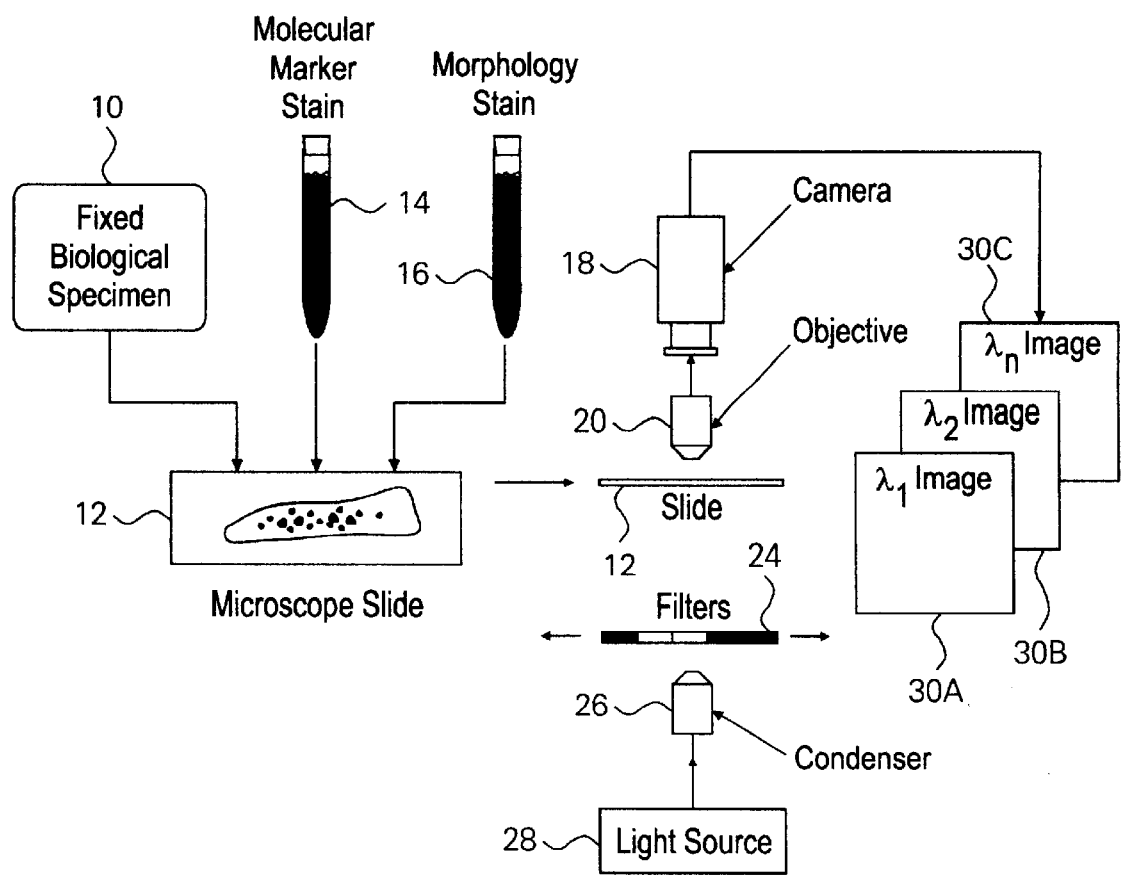
FIG. 1 shows a system for collecting images at multiple illumination wavelengths.

The invention relates to the general field variously referred to as computer vision, machine vision, visual intelligence, or computational image analysis as applied to biological specimens using light absorbing dyes. In the instruments using this technology, a human observer's vision and interpretation of what is seen is replaced by the collection of digitized images and the calculation of parameters that express the information content of those images. Human observers often derive information from the color of what is viewed. Color is perceived when the light reaching the observer's retina varies in intensity over the visible spectrum. Chromogens attached to a specimen viewed under a microscope produce a color by absorbing the light at that color's complementary wavelength. The observer sees blue, for instance, when yellow light is heavily absorbed. By using a chromogen that absorbs yellow light as the dye component of a molecular marker, the objects containing the target molecules appear blue. The invention provides a method and apparatus for making this chromatic information available to image processing processes of a visual intelligence instrument. Fundamental to the invention is the collection of images in which the image contrast is produced by absorption of light transmitted through the specimen and in which each image utilizes measurements of light at a particular narrow wavelength band. FIG. 1 shows one example embodiment for implementing this method.

Now refer to FIG. 1, which shows a system for collecting images at one or multiple illumination wavelengths and generating a biological specimen analysis score. A fixed biological specimen 10 is deposited on a microscope slide to create a specimen slide 12. The microscope slide 12 may be a cervical cancer smear, blood sample, sputum specimen, urine, bone marrow, spinal fluid or any other cellular biological specimen. During preparation of the microscope slide 12, the fixed biological specimen 10 is stained with a molecular marker stain 14. The molecular marker stain 14 may comprise an antibody and associated dye or a nucleic acid and associated dye or any other molecular light absorbing dye. Also during preparation of the microscope specimen slide 12, a fixed biological specimen 10 is stained with a morphology stain 16. The morphology stain is comprised of a light absorbing dye such as a Pap stain, Romanowski stain, Wright-Giemsa or any other cellular morphology stain. See *Biological Stains*, by H. J. Conn, 9th edition, Williams & Wilkins Co., for information on morphology stains.

A monochromatic camera 18 receives an image from an objective 20 of the slide 12 in a conventional manner. The filters 24 filters light from light source 28 received through condenser 26. During operation, multiple images of the slide 12 are taken using different filters. The multiple filters may be automatically moved into position to take the multiple images in a conventional manner or an electronically controlled variable filter may be used when taking the multiple images, each image being taken at a different wavelength. The camera 18 generates a number of images shown as images 30A–30C. Image 30A corresponds to an image taken with a filter at a first wavelength. Image 30B corresponds to an image taken with a filter at a second wavelength. Image 30C corresponds to an image taken with a filter at an nth wavelength. This system is shown in more detail as the AUTOPAP from NeoPath, Inc. of Redmond, Wash. Specifically, the structure and operation of the image processing elements of the system are shown in more detail in FIGS. 15A, 15B and 15C.

In operation, light from the broadband incandescent light source 28 passes through the filters 24 on its path to the specimen slide 12. This illumination is focused by the condenser 26 onto the plane of the specimen slide 12. The light transmitted through the specimen slide 12 is collected by the objective 20, which forms a well focused image at the face of the electronic camera 18. The camera 18 captures an image at each illumination wavelength of a set of illumination wavelengths. Multiple filters or a single filter having a variable center wavelength in its passband may provide the illumination wavelengths. The captured images 30A, 30B and 30C are either immediately processed or stored in an electronic memory or other storage medium for later processing.

With this hardware configuration, it is important that the microscope stage, shown in more detail in FIG. 15C, optical components, and camera 18 are all effectively isolated from vibration so that the captured images are properly aligned with one another. The maximum spatial offset between images taken of the same location with different filters should be held to less than a fraction of a pixel width.

It is also important that all of the images for a field of view are well focused. See assignee's United States Patents and co-pending patent applications incorporated by reference herein. The system must have stability of the microscope stage in the vertical direction, but also be able to eliminate the effects of chromatic aberrations in the image forming optics. Note that the term "field of view" refers to a region in the specimen with dimensions defined by the active area of the camera 18 divided by the magnification of the image-forming optics. Multiple images will be collected from a single field of view by keeping the stage stationary between image capture events.

A variety of alternative configurations of the apparatus are equally applicable to the invention. The wavelength selection can be accomplished in the light path between the objective and the camera, for example. Furthermore, separate cameras, each having its own optical filter at a particular wavelength can be utilized to allow simultaneous collection of multiple images.

The camera 18 may be electronic, using a charge-coupled device array or other type of electronic light sensor, or may be a film camera, in which case the storage medium is photographic film. Furthermore, those skilled in the art will recognize that the wavelength separation in the image collection system may be accomplished through the use of prisms or gratings rather than light absorbing filters.

Figure 2:
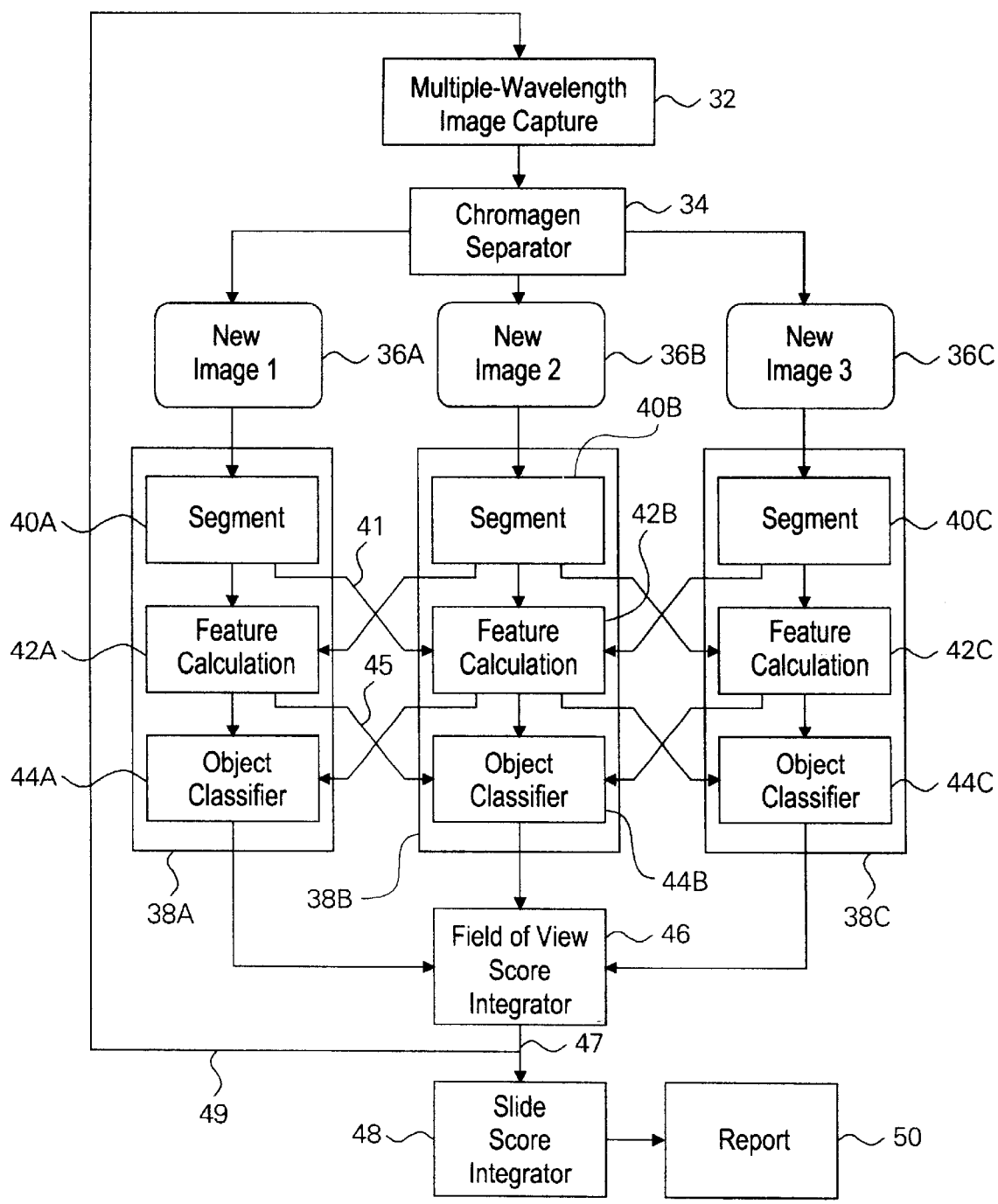
FIG. 2 shows a process flow diagram for the automatic generation of a biological specimen analysis score from one or more wavelength images.
Figure 3:
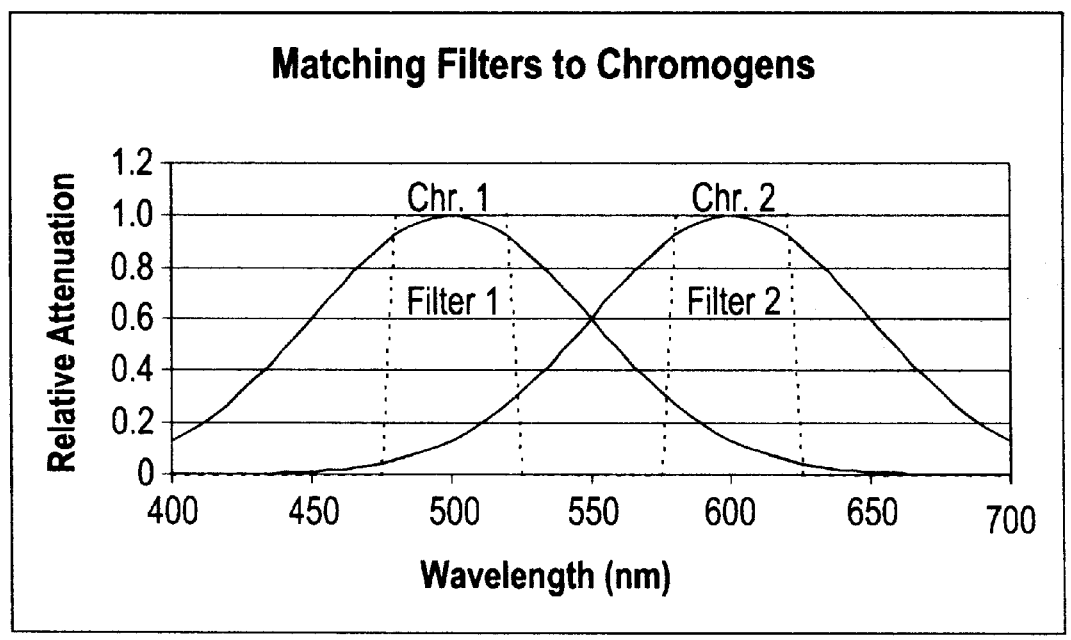
FIG. 3 shows a graph of relative attenuation to wavelength that may be used to match optical filters to chromogens.

Refer now to FIG. 2 which shows the apparatus and method of the invention to generate a slide score from multiple images of a slide taken at different wavelengths. In step 32, the process starts by capturing multiple images of the slide 12 at wavelengths specifically designed to match to a chromogen. This matching relationship is shown in FIG. 3 as a wavelength vs. relative attenuation diagram. Chromogen 1 is matched to filter 1. It will be noted that some of the signal from chromogen 2 will also be passed by filter 1.

The general configuration of the image processing of the invention is shown in FIG. 2. Images collected at multiple wavelengths are translated into a second set of images, new image 1 36A, new image 2 36B and new image N 36C, by the chromogen separator 34. The chromogen separator 34 is a computational tool that will be described in detail herein. Each of the new images, new image 1 36A, new image 2

36B and new image N 36C, is processed in an information processing branch 38A, 38B or 38C to extract information content. Each processing branch 38A, 38B and 38C is comprised of the general operations of object segmentation 40A, 40B and 40C, object feature calculation 42A, 42B and 42C, object type classification 44A, 44B and 44C. See assignee's U.S. Patents and assignee's copending U.S. patent application incorporated by reference hereto for more detail on these operations. Each processing branch also performs specimen scoring. The specimen score from each branch 38A, 38B and 38C is integrated in field of view score integrator 46. In one embodiment, object segmentation may be accomplished by rule-based processes or pattern matching. Object classification may be accomplished using methods that include, but are not limited to, rule-based decision trees and, alternatively, artificial neural networks. Processing may occur in the space domain, the spatial frequency domain, or both.

The image processing of the invention branches out beyond the chromogen separator to analyze each image separately. However, cross-connections shown by connection 41 between branches 38A and 38B, for example, may serve to allow the segmentation masks for one image to select pixels for feature calculation in another branch. Features from a first branch may also modify the outcome of processing in a second branch. Connection 45 provides one such example of features from branch 42A modifying the processing of object classifier 44B.

For example, assume that Image 1 is used for morphological cell type classification and that Image 2 is used for searching for a molecular marker. Once a cell of a particular type is localized and identified, the pixel locations inside of that cell might be sent to the Image 2 processor to check for the presence or absence of the molecular marker. Conversely, upon detection of a strong molecular marker in Image 2, the Image 2 processor might query the Image 1 processor to identify the type of cell showing the marker.

The outcome of processing in each branch of the classifier is integrated by FOV score integrator 46 into an outcome 47 for the field of view. Multiple fields of view, shown by flow line 49 indicating that the next field of view is to be processed, are collected and processed until the useful area of the specimen has been examined. The parameters, resulting from the FOV score integrator for a number of FOVs, stored for the collection of fields of view are then integrated by slide score integrator 48 into an outcome for the entire specimen reported to the user on report 50.

Figure 4:
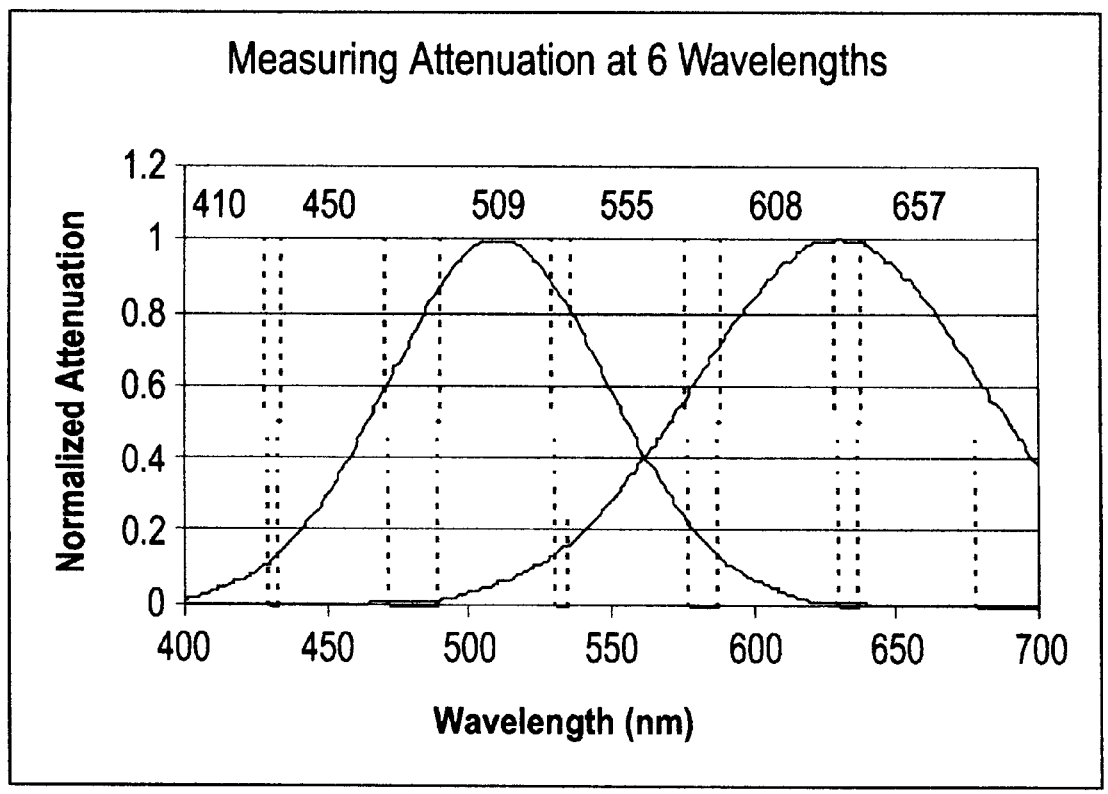
FIG. 4 shows a graph of normalized attenuation to wavelength for six wavelengths.
Figure 5:
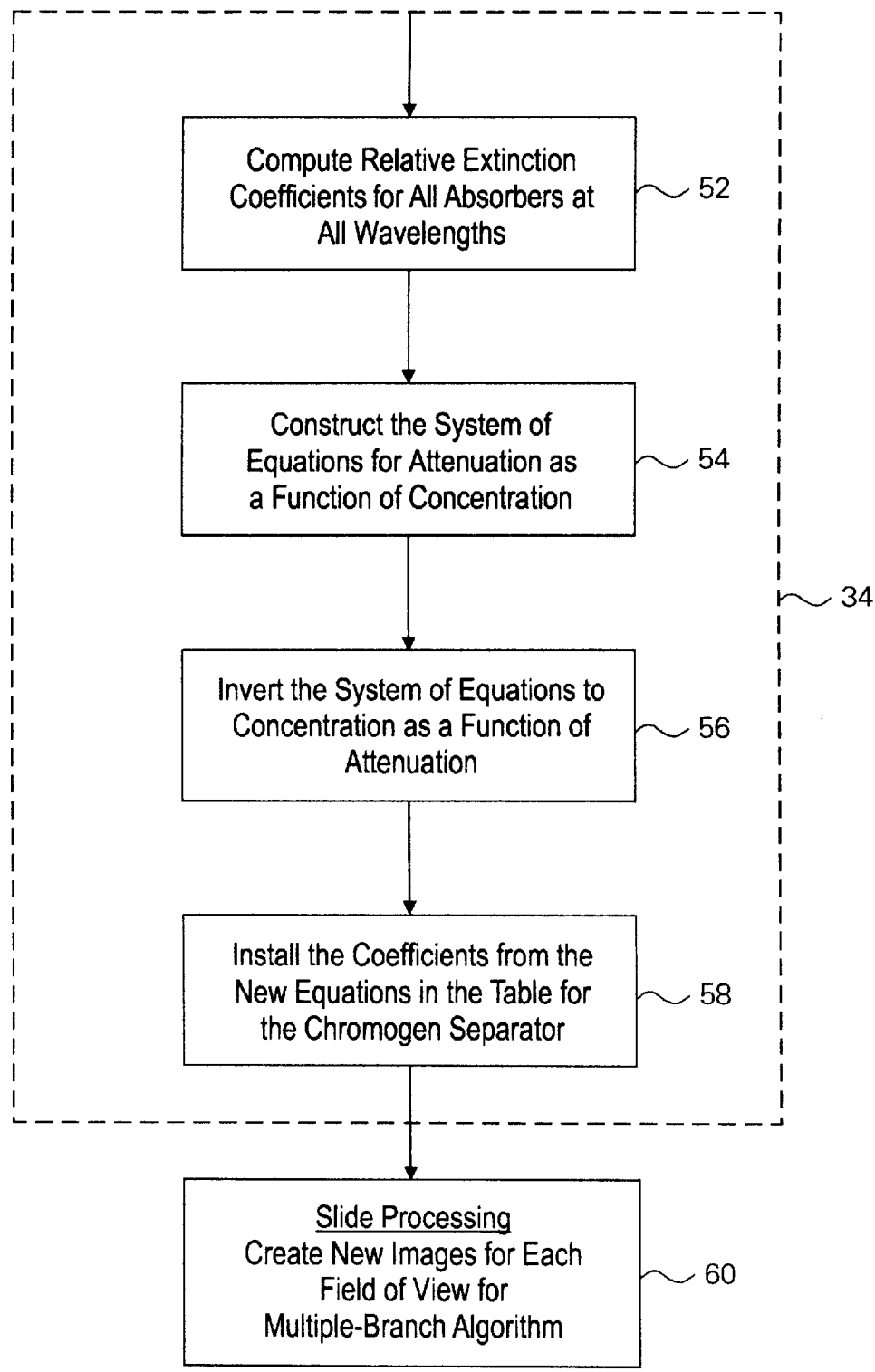
FIG. 5 shows a process flow diagram for the determination of new images based on chromogen separation.

Refer now to FIG. 5 which shows the detailed processing steps of the chromogen separator 34 to generate information useful for creating new images for each field of view where the new images have enhanced morphological information and/or enhanced molecular marker information. The process starts by computing the relative extinction coefficients for all chromogens at all wavelengths in step 52. For example, when automatically analyzing a specimen with two chromogens at six wavelengths, as depicted in FIG. 4, the relative extinction coefficients from chromogen 1 at the six wavelengths is computed and the relative extinction coefficients for chromogen 2 at the six wavelengths is computed. Details of the computation are shown below. As will be shown, in one embodiment, the extinction coefficients may be computed before analysis of a specimen for a system of chromogen and wavelength processes. This is known as "offline" processing. In an alternate embodiment, these extinction coefficients may be computed from a specimen. This is known as "online" processing. Those skilled in the art will recognize that if the relative extinction coefficients are computed offline, then the chromogen separator will use the values previously stored for system chromogens and wavelengths.

After the relative extinction coefficients are computed by either method, the process flows to step 54 to construct a system of equations for attenuation as a function of concentration.

The process then flows to step 56 to invert the system of equations to solve for concentration. Knowing the concentration at a pixel location and the relative extinction coefficients for a chromogen at a particular wavelength permits the construction of a new image by creating a table of coefficients, examples of which are shown in Table 1 and Table 2 in step 58. In step 60, the new images are created. This processing will now be described in more detail.

The first step in the optimization of the performance of the chromogen separator 34 is the selection of chemical dyes to meet the requirements of a particular application and the selection of optical filters 24 to match their absorption characteristics. A large number of chemical dyes for biological applications are commercially available, and their manufacturers provide information on their absorption spectra. Optical filters can then be selected to match the absorption peaks of the chromogens, as shown in FIG. 3.

Electronic images are typically stored using binary or integer data formats and have quantization accuracy limited by the number of bits used to digitize the camera 18 output. Each pixel in the image is assigned a value on the scale of possible values, which is known as the grayscale. For the purpose of this invention, it is important that the grayscale value be directly proportional to the light intensity reaching the face of the camera 18, as is the case for charge-coupled device cameras. Any deviation from this direct proportionality to intensity, such as might be introduced by nonlinearity in the signal processing hardware, should be corrected before the images can be used in the manner described herein. Once corrected, the grayscale value can be expressed in terms of attenuation in the specimen, as follows:

$$G_n(i,j) = G_n(0) \cdot e^{-\alpha(i,j)} \quad (1)$$

where:

n=index identifying filter with center wavelength $\lambda_n$;

$G_n(i,j)$=grayscale value for pixel i,j in image collected at $\lambda_n$;

$G_n(0)$=grayscale value for zero attenuation in specimen using filter n; and $\alpha(i,j)$=attenuation coefficient for pixel i,j.

$$\alpha_n(i, j) = -\ln\left(\frac{G_n(i, j)}{G_n(0)}\right) \quad (1.1)$$

where n=index identifying filter with center wavelength $\lambda_n$;

$G_n(i,j)$=grayscale value for pixel i,j in image collected at $\lambda_n$;

$G_n(0)$=grayscale value for zero attenuation in specimen using filter n; and $\alpha_n(i,j)$=attenuation coefficient for pixel i,j.

The image capture system is capable of measuring the attenuation over a finite range of values. This range is called the dynamic range of the imaging system.

A first approximation of the range of measurable values for α is found by considering the number of bits in the camera signal digitizer or the image storage data format, whichever is smaller, and the zero-attenuation grayscale value:

$$\alpha_{max} = -\ln \frac{1}{G_n(0)} \quad (3)$$

This equation derives from the knowledge that the smallest grayscale value meaningful for attenuation calculation is 1. If the image data is stored in 8 bits, then the maximum value of $G_n(0)$ is 255, and the maximum value of α is 5.54. In practice, however, electronic noise, digitizer uncertainty, and photon count would set a minimum useful grayscale value higher than 1, and $G_n(\mathbf{0})$ would be set to a value somewhat less than the full scale of the digitizer. A practical range for measurements of a in an 8-bit system is from 0 to 4.0.

In order for the chromogen separation method that is central to the invention to function properly, the light transmitted through the specimen and focused on the light detecting surface of the camera must remain within the dynamic range of the camera. That is, the light transmitted through clear regions of the specimen must not saturate the camera or the signal processing electronics. Also, the light transmitted through the most attenuating regions of the specimen must not fall below the noise floor or the first level of digitization, whichever is larger.

Furthermore, the value of G(0) must be known to an accuracy of a few gray levels for every image. Because both the efficiency of light transmission along the optical path for image formation in the system and the sensitivity of the camera may vary with wavelength, a method is required either to measure G(0) for each image, or to tightly regulate it as wavelength is varied. If the wavelength dependence is substantial, it is preferable to maintain a constant G(0) by varying the light level in the illuminator. This approach maintains the imaging system dynamic range. To maintain G(0) at a constant level, correction parameters calculated and stored using an instrument calibration method will need to be used to vary the illuminator light intensity as wavelength is varied.

More than one chromogen may contribute to the absorption of light inside the passband of a given filter. In fact, since absorption dyes generally display absorption that spreads over a large fraction of the visible light spectrum, this effect is likely to happen whenever multiple chromogens are present in a specimen. In the case where this overlap of absorption curves occurs inside of a filter band, the attenuation can be decomposed into component parts:

$$\alpha_n(i,j) = \alpha_{1,n}(i,j) + \alpha_{2,n}(i,j) + \ldots + \alpha_{m,n}(i,j) \quad (4)$$

where:

n=index for filter centered at $\lambda_n$; and m=index identifying the chromogen.

The process then flows to step 54 to construct a system of equations for attenuation as a function of concentration. It is known that the attenuation coefficient for a given thickness of absorbing material is directly proportional to the concentration of the chromogen in that material. The constant of proportionality is known as the extinction coefficient, ε. The attenuation equation, then, can be expanded as follows:

$$\alpha_n(i,j) = \epsilon_{1,n} C_1(i,j) + \epsilon_{2,n} C_2(i,j) + \ldots + \epsilon_{m,n} C_m(i,j) \quad (5)$$

where:

$\epsilon_{m,n}$ extinction coefficient for chromogen m and wavelength n; and $C_m(i,j)$=concentration of chromogen m at pixel location i,j.

The concepts of concentration and extinction coefficient will be used in a relative sense, and the specimen thickness will be assumed to be uniform and not considered in the derivations to follow. We will arbitrarily limit the extinction coefficients to a range from 0 to 1.0. The concentration will also be known only in a relative sense as the ratio α/ε.

Figure 6:
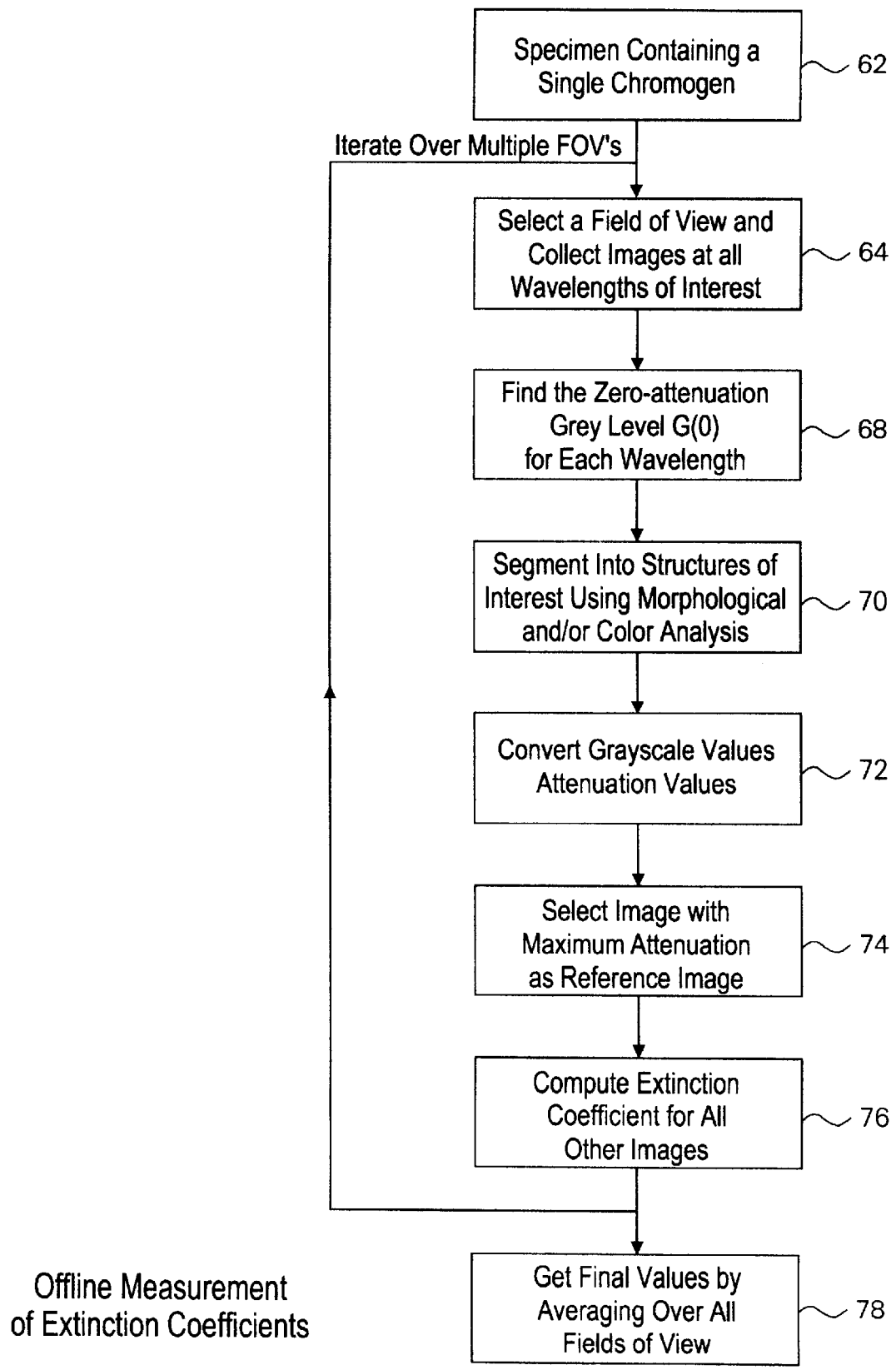
FIG. 6 shows a process flow diagram for the offline measurement of extinction coefficients from a specimen containing a single chromogen.

Refer now to FIG. 6 which shows the method of the invention to determine extinction coefficients from specimen with a single chromogen. A set of specimens, each specimen containing only one chromogen from the stain formula, is prepared. Each specimen is scanned, in step 62, using a microscope with the capability of capturing images at multiple wavelengths for analysis. The particular chromogen under examination will stain certain parts of the specimen. The image showing the most attenuation is chosen, in step 64, as the reference image. In step 68 the zero attenuation Gray level for each wavelength is found. The extinction coefficient for the images at each of the other wavelengths will be measured relative to the reference image. The computation must be restricted to pixel locations where the chromogen is present. A segmentation mask 70 can be generated using one of a variety of methods.

For example, given that the only absorption in the image is by the chromogen, a simple threshold can be applied to the grayscale values in the reference image to create the mask. Alternatively, images from red, green, and blue filters can be used to generate color images. These color images could be converted to the Hue, Saturation, and Value (HSV) format using a method well known in the art. The segmentation mask could then be generated by selecting pixels having hue and saturation values within certain ranges that match the spectral behavior of the chromogen. The hue window selects the basic color of the chromogen, while the saturation selects for how much white light is mixed with that color. A light blue, for example, scores low on the saturation scale, whereas a deep blue scores high on the saturation scale.

When performing the extinction coefficient calculation, the grayscale values of all of the images are converted to attenuation values in step 72. The reference wavelength is then assigned an extinction coefficient of 1.0 in step 74, and the relative extinction coefficients for the other wavelengths, in step 76, are computed as the ratio of attenuation values as follows:

$$\epsilon_{sec} = \frac{\epsilon[A_{sec}]}{\epsilon[A_{ref}]} \quad (6)$$

where:

$A_{sec}$=attenuation in secondary image, a random variable;

$A_{ref}$=attenuation in the reference image, a random variable; and

E[X]=expectation operator, returns the average of random variable X.

The segmentation mask defines the domains of the random variables, $A_{sec}$ and $A_{ref}$.

The extinction coefficient calculation is repeated over a number of fields of view of the specimen and the values are averaged in step 78 to improve accuracy.

Figure 7:
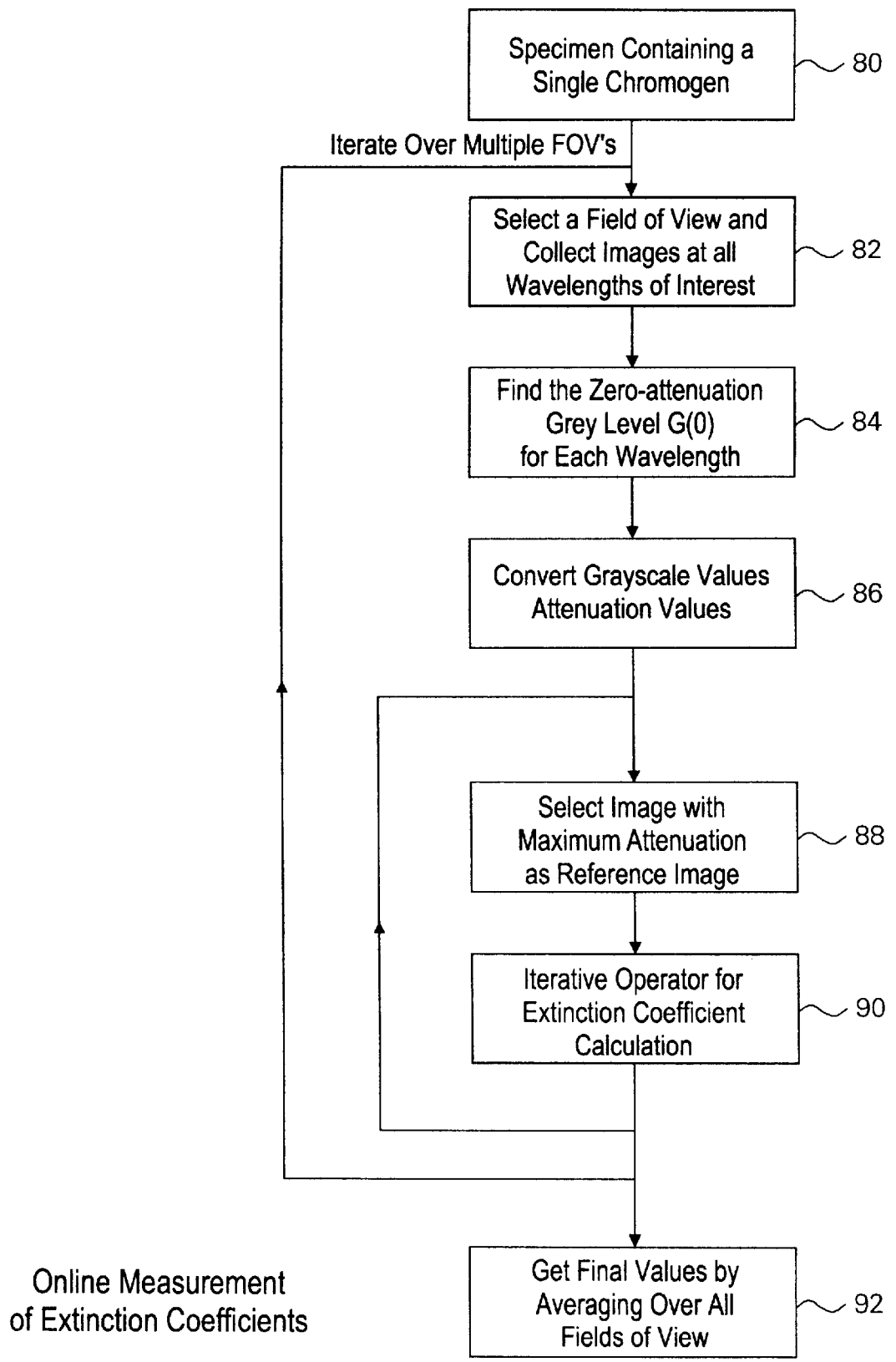
FIG. 7 shows a process flow diagram for the online measurement of extinction coefficients from a specimen containing multiple chromogens.

Now refer to FIG. 7 which shows a process flow diagram to perform online measurement of extinction coefficients. In this case, the extinction coefficients are computed within the instrument that will be used for the actual automated microscopy. The specimen will contain all of the chromogens in the dye formula 80. All of the steps in the measurement of the extinction coefficient are the same as for the offline method, except for the generation of the segmentation mask. In step 82 the process selects a field of view and collects images at all wavelengths of interest. In step 84, the zero attenuation gray level is found for each wavelength. In step 86 grayscale values are converted into attenuation values. For the online method, a unique segmentation mask is created for each of the chromogens in the specimen using an iterative segmentation process 90 based on cross-correlation of the attenuation values. In step 88, the process selects an image with maximum attenuation as a reference image. The reference image for each chromogen is an image captured using the optical filter matched to the known peak of that chromogen. Final values are obtained by averaging over all fields of view in step 92.

Figure 8:
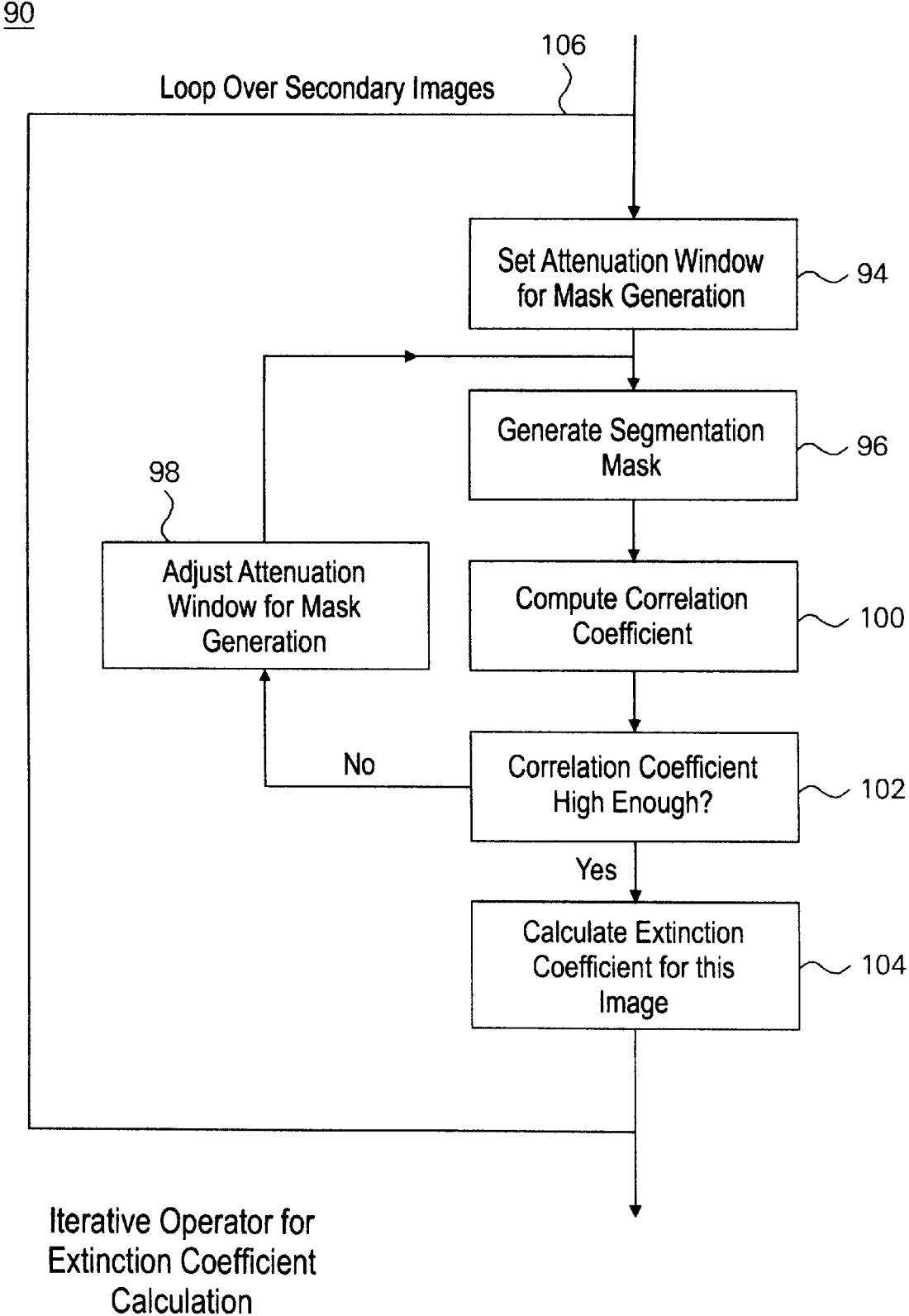
FIG. 8 shows a process flow diagram of an iterative operator for extinction coefficient calculation.

Refer now to FIG. 8 which shows the method of the invention to iteratively determine the extinction coefficient. The iterative segmentation process 90 operates by selecting pixels within a range of ratios of the reference attenuation and the secondary attenuation. In step 94, an attenuation window for mask generation is set. In step 96, a mask is generated. The range of ratios is modified to increase the correlation coefficient between the reference image pixels within the mask and their counterparts in the secondary image. In step 100, correlation coefficients are computed. The cross-correlation calculations are as follows:

$$\rho(A_1, A_2) = \frac{Cov[A_1, A_2]}{\sqrt{Var(A_1) \cdot Var(A_2)}} \quad (7)$$

where:

$$Cov[A_1, A_2] = E[A_1 \cdot A_2] - E[A_1]E[A_2] \ Var[A_1] = E[A_1^2] - (E[A_1])^2 \ Var[A_2] = E[A_2^2] - (E[A_2])^2 \quad (8)$$

$A_n$=attenuation at wavelength n, a random variable.

Note that $A_1$ is the random variable that includes all of the values of $\alpha(i,j)$ in image 1. Similarly, $A_2$ is the random variable for $\alpha(i,j)$ in image 2. E[x] is the "expectation value" of the random variable X, which is computed as the average of the variable x. In the above equations, $E[A_n]$ is the average attenuation value for all the pixels of the image for wavelength n inside the segmentation mask.

The meaning of the correlation coefficient can be understood by considering a single pixel location in the specimen that is stained with Chromogen 1, which has its absorption peak at Wavelength 1. If Chromogen 1 also causes absorption at Wavelength 2, but not at Wavelength 3, then as the concentration of Chromogen 1 is increased, the pixel will get darker in both Image 1 and Image 2, but not in Image 3. Now, if we pick out all of the pixels in a field of view that contain Chromogen 1 and convert their grayscale values to attenuation values, we will find that there is a high correlation between the attenuation in Images 1 and 2, but a low correlation between either of Images 1 and 2 and Image 3. In the iterative segmentation operator, we turn the problem around and search for high correlations to help us pick out the pixels stained by a particular chromogen.

The iterative loop can be controlled using an error minimization scheme such as Newton's Method to modify the attenuation ratio on each successive pass through the process in such a way as to converge on a particular value for the correlation coefficient. In step 98, the process adjusts the attenuation window for mask generation and returns to step 96 to generate a mask. Upon convergence, the mask will contain only those pixels that have a high concentration of the chromogen in both the reference and the secondary image, in step 102. Certain criteria should be placed on the convergence, however. First, a considerable number of pixels should be retained in the mask, and, second, a high value of correlation should have been accomplished. Reasonable values for these limits might be 1000 pixels in the mask and a correlation coefficient above 0.85, although these criteria will need to be optimized through experimentation.

Using the segmentation mask provided by the iterative correlation algorithm, the extinction coefficient is calculated in step 104 as follows:

$$\varepsilon_{f,m,n} = \frac{E[A_{sec}]}{E[A_{ref}]} \quad (9)$$

where:

$A_{sec}$=attenuation in secondary image, a random variable;

$A_{ref}$=attenuation in the reference image, a random variable;

f=index for the field of view;

m=index for the chromogen; and n=index for the secondary wavelength.

The extinction coefficient process is repeated 106 for all of the chromogens and their associated reference and secondary wavelengths for each of a set of fields of view. The number of fields of view is chosen to improve the accuracy of the extinction coefficient measurements. The number of fields of view attempted will increase if the iterative operator fails to meet the convergence criteria. This event will be encountered whenever the field of view lacks the requisite amount of material stained by the chromogens of interest.

Note that it may be desirable to use conventional morphological segmentation to generate an initial mask and to further reduce that mask using the iterative correlation operator. For example, if a chromogen is know to stain nuclei strongly, morphological segmentation could be used to selected all objects meeting the shape and size criteria for nuclei. The mask of all pixels representing nuclei could then be submitted to the iterative correlation operator to further reduce the mask to the pixels in nuclei stained by that chromogen.

As shown in FIG. 5, upon completion of the cross-correlation between images with neighboring wavelengths, the relative extinction coefficients are installed in a set of equations for the attenuation values for each pixel at every wavelength. The following set of equations is written for the general case of "m" chromogens and "n" wave-lengths:

$$\alpha_1(i,j) = \epsilon_{1,1} \cdot C_1(i,j) + \epsilon_{2,1} \cdot C_2(i,j) + \ldots + \epsilon_{m,1} \cdot C_m(i,j)$$

$$\alpha_2(i,j) = \epsilon_{1,2} \cdot C_1(i,j) + \epsilon_{2,2} \cdot C_2(i,j) + \ldots + \epsilon_{m,2} \cdot C_m(i,j)$$

$$\alpha_n(i,j) = \epsilon_{1,n} \cdot C_1(i,j) + \epsilon_{2,n} \cdot C_2(i,j) + \ldots + \epsilon_{m,n} \cdot C_m(i,j)$$

where:

(i,j) are the pixel coordinates;

$\alpha_n(i,j)$=attenuation at wavelength "n" for the pixel (i,j);

$\epsilon_{m,n}$=relative extinction coefficient for chromogen "m" at wavelength "n"; and $C_m(i,j)$=relative concentration of chromogen "m" for pixel (i,j).

Using a method of linear algebra such as the Gauss-Jordan Elimination, this set of equations is inverted, in step 56, to yield a new system of equations for the concentration as a function of attenuation:

$$C_1(i,j) = k_{1,1} \cdot \alpha_1(i,j) + k_{1,2} \cdot \alpha_2(i,j) + \ldots + k_{1,n} \cdot \alpha_n(i,j) \quad (10)$$

$$C_2(i,j) = k_{2,1} \cdot \alpha_1(i,j) + k_{2,2} \cdot \alpha_2(i,j) + \ldots + k_{2,n} \cdot \alpha_n(i,j)$$

$$C_m(i,j) = k_{m,1} \cdot \alpha_1(i,j) + k_{m,2} \cdot \alpha_2(i,j) + \ldots + k_{m,n} \cdot \alpha_n(i,j)$$

where:

(i,j) are the pixel coordinates;

$\alpha_n(i,j)$=attenuation at wavelength "n" for the pixel (i,j);

$k_{m,n}$=coefficients from matrix inversions; and $C_m(i,j)$=relative concentration of chromogen "m" for pixel (i,j).

In step 58 coefficients from the new equations in the table for the dye separator are installed. Note that the process of developing the concentration equations is performed at most once per specimen slide. However, during slide processing, new images are created for each field of view. If it is desired to analyze an image whose contrast is created only by the molecular marker, for example, then a new image is generated by subtracting the contributions from the morphology chromogens from the image captured using the filter matched to the molecular marker. A new morphology image might also be created with the molecular marker removed. For example, if we would like an image that displays only the absorption from chromogen 1, which is centered on wavelength 1, we remove the contributions from chromogens 2 and 3 as follows:

$$\alpha'_1(i,j) = \alpha_1(i,j) - \epsilon_{2,1} \cdot C_2(i,j) - \epsilon_{3,1} \cdot C_3(i,j) \quad (11)$$

A new image is generated in step 60 from the calculated attenuation values using a default grayscale value N(0) for the full white level, as follows:

$$G(i,j) = N(0) \cdot e^{-\alpha'_1(i,j)} \quad (12)$$

where:

G(i,j)=gray level of pixel (i,j) in new image;

N(0)=gray level for the hypothetical clear area; and $\alpha'_1(i,j)$=computed attenuation after other chromogens removed.

The gray level of a hypothetical clear area N(0) is chosen based on the range of the grayscale values. For example an eight bit (0–255 range) may be assigned an N(0) of 238. The choice of chromogens retained in a new image will be made with the goal of improving object segmentation or strengthening particular object features to improve the performance of the image analysis algorithms.

Alternatively, a new image may be created by varying extinction coefficients.

$$\alpha''_1(i,j) = \epsilon_{1,1} \cdot C_1(i,j) + \epsilon''_{2,1} \cdot C_2(i,j) + \epsilon_{3,1} \cdot C_3(i,j) \quad (11.1)$$

For example, if the extinction coefficient $\epsilon_{2,1}$ is changed from its measured value to a new $\epsilon''_{2,1}$, determined experimentally based on the behavior of a hypothetical chromogen, the new image would reflect this behavior. The grayscale value is adjusted in a similar manner to equation 12.

An alternative new image is generated from the calculated attenuation values using a default grayscale value N(0) for the full white level, as follows:

$$G(i,j) = N(0) \cdot e^{-\alpha''_1(i,j)} \quad (12.1)$$

where:

G(i,j)=gray level of pixel (i,j) in new image;

N(0) gray level for the hypothetical clear area; and $\alpha''_1(i,j)$=attenuation for hypothetical chromogen.

In order to demonstrate the principles outlined above, images were collected at six wavelengths for a field of view from a cervical smear containing Papanicolaou stain. FIG. 4 illustrates the selection of filters used. Four active dyes comprise the Papanicolaou mixture. Their names and their wavelengths of peak absorption are as follows: Orange G, 480 nm; Eosin Y, 520 nm; hematoxylin, 560 nm; and Light Green SF Yellowish, 630 nm. A fifth component, Bismarck Brown, has been shown to fail to stain cells.

In the example of FIG. 4, a specimen is stained with two dyes. The first dye absorbs most of its light at around 509 nm. The second dye absorbs at 630 nm. The system will capture six images at six wavelengths. This is basic information used to separate the dyes.

The four active dyes combine to give absorption widely distributed in wavelength, with two major components. The first, which we will refer to as Chromogen 1, peaks around 510 nm. The second, Chromogen 2, peaks around 630 nm. The exact shape of the distributions and location of the peaks is variable. The hypothetical distributions in FIG. 4 are presented to illustrate the concept of a two-component Chromogen system. It should also be noted that neither of the two components is limited to just the nucleus or just the cytoplasm. Both chromogens stain both nuclei and cytoplasm. Cytoplasm staining, furthermore, is dependent on the internal pH of the cell, which modulates the ratio of absorption between the shorter and the longer wavelengths.

Figure 9:
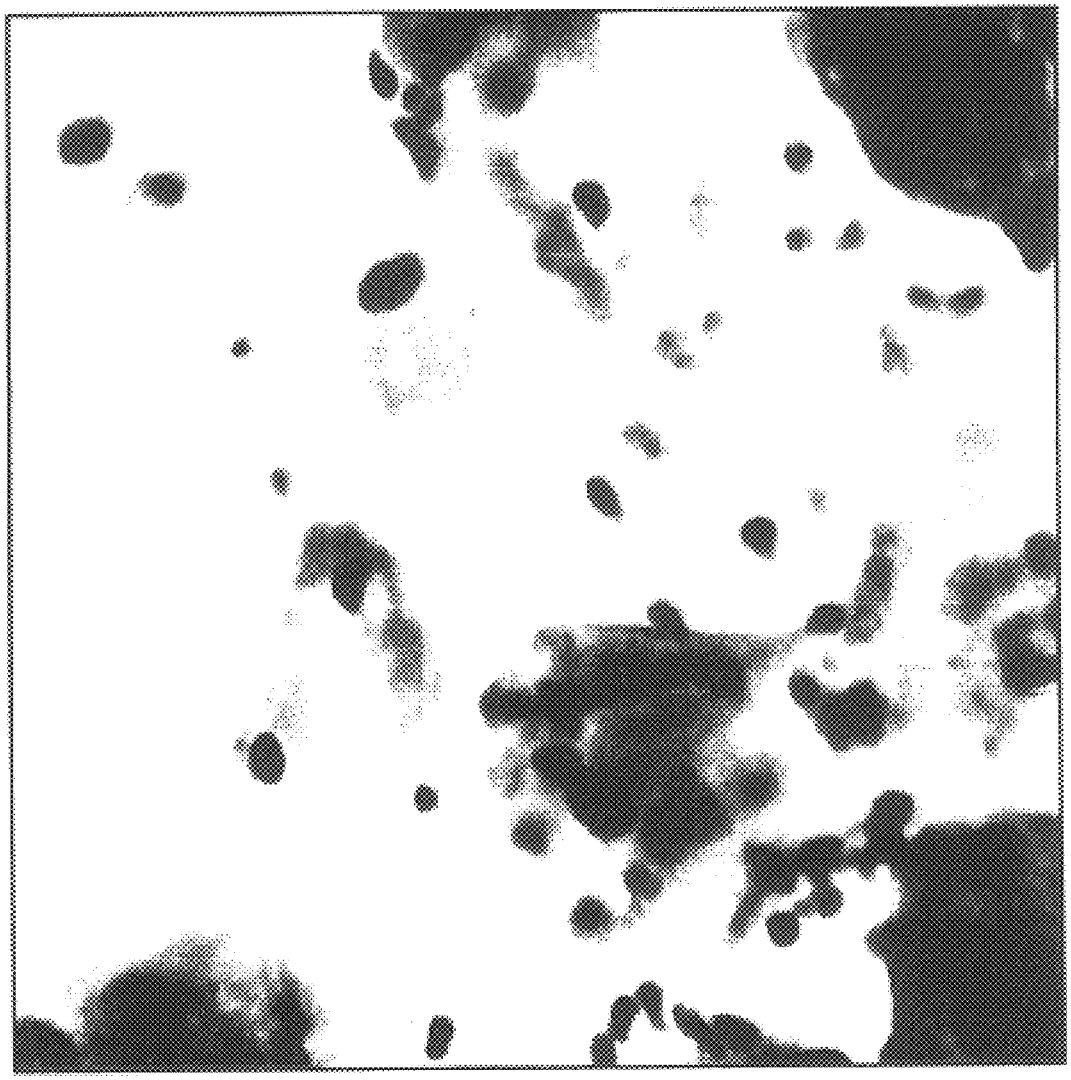
FIG. 9 shows an image of a biological specimen collected using a 509 nm filter.
Figure 10:
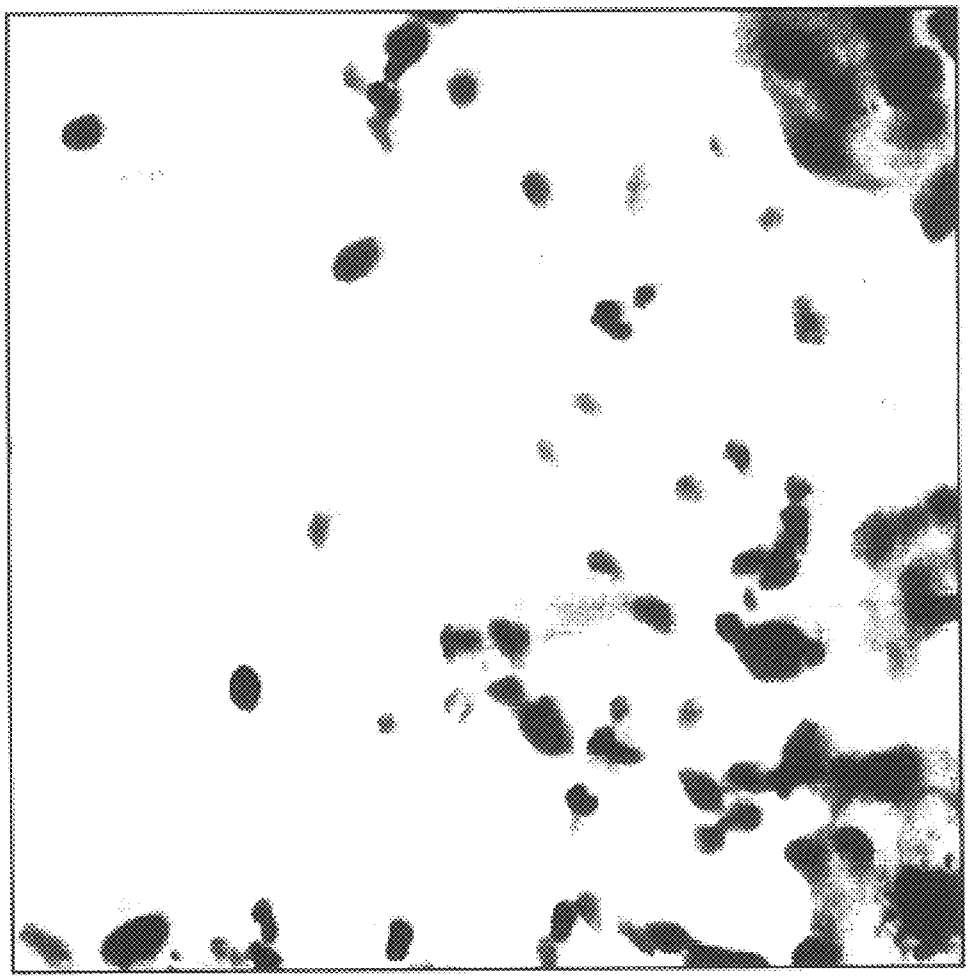
FIG. 10 shows an image of a biological specimen collected using a 555 nm filter.
Figure 11:
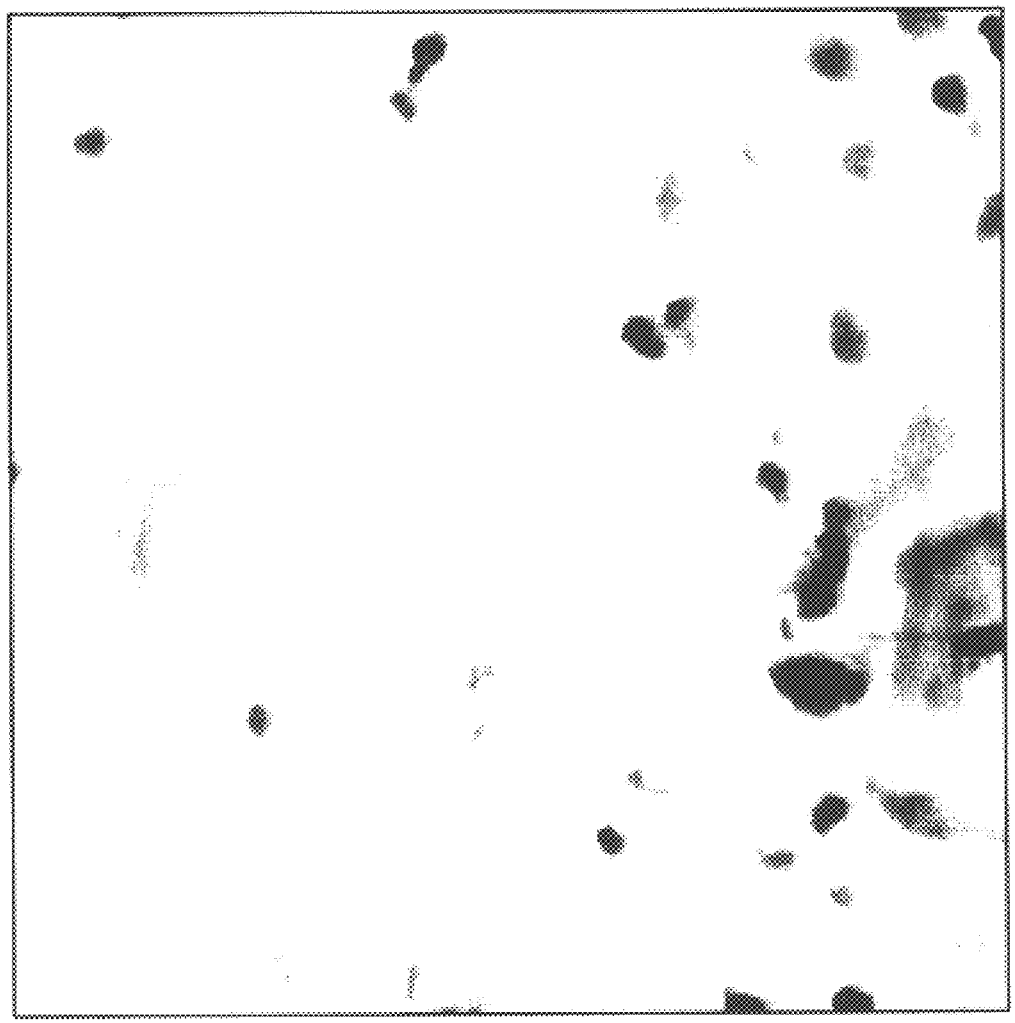
FIG. 11 shows an image of a biological specimen collected using a 608 nm filter.

FIGS. 9, 10 and 11 show images collected at center wavelengths of 509, 555, and 608 nm, respectively, with the instrument shown in FIG. 1. The system is known to be linear and of sufficient dynamic range to quantify attenuation over the full range of intensity of the light transmitted by the specimen. The grayscale level for the clear regions of the specimen were found for each wavelength, allowing the computation of attenuation values for all pixels at all three wavelengths.

FIG. 9 is an image of a slide using a 509 nm filter. FIGS. 9, 10 and show the same field of view with images collected at three different wavelengths. Note that the contrast changes from wavelength to wavelength. The figures illustrate the effects of two different dyes staining both the nucleus and the cytoplasm, and the property that as the wavelength changes the contrast in those structures also changes. This gives information about the behavior of the two dye. This information is used in designing the chromogen separator.

Figure 12:
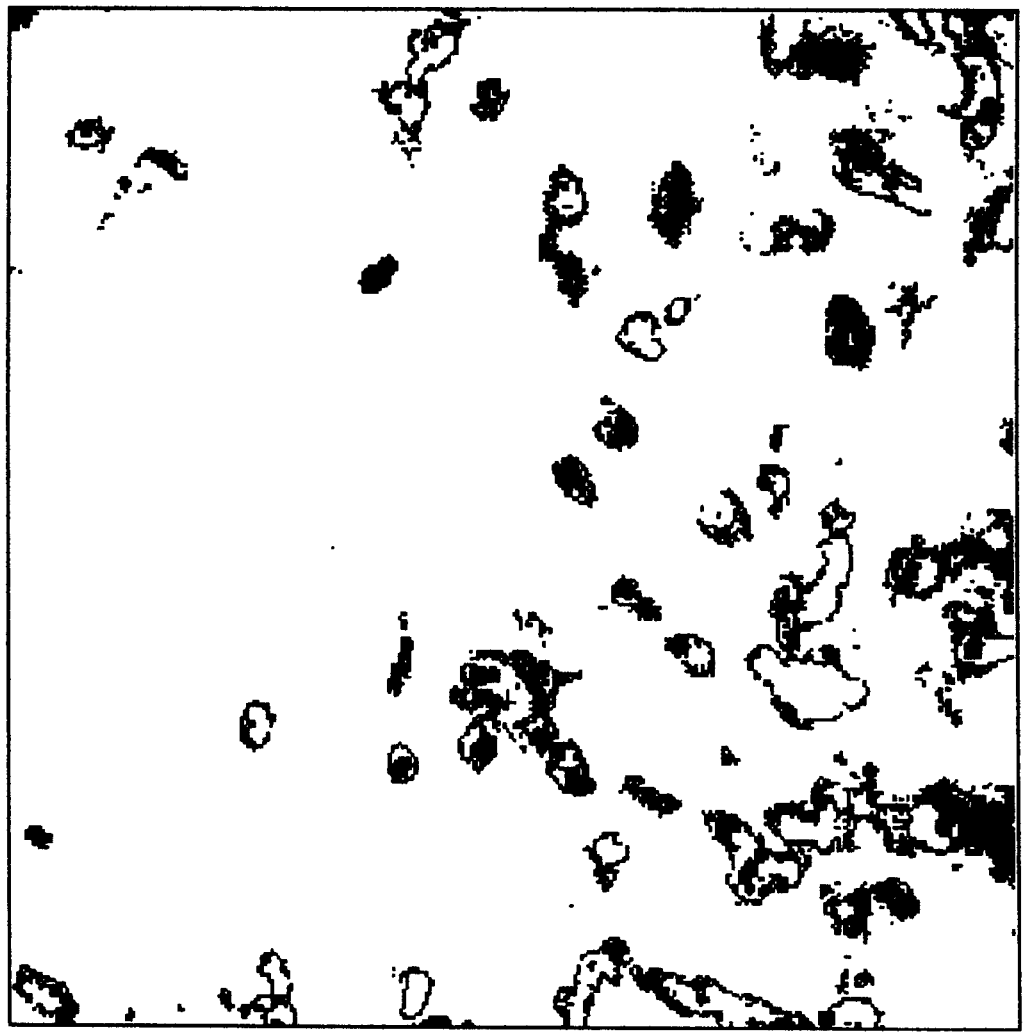
FIG. 12 shows a mask for selecting nuclei.

Now refer to FIG. 12, FIG. 12 illustrates the next step in the design of the chromogen separator. FIG. 12 demonstrates the behavior of the dye. Specialized masks are developed for separating one structure from another in the images. By separating nuclei from the rest of the image, the behavior of the dyes in the nuclei can be analyzed. FIG. 12 shows the mask for selecting nuclei. As shown in Tables 1 and 2, calculations can be made of the relative extinction coefficients of the various dyes in the sample.

Figure 13:
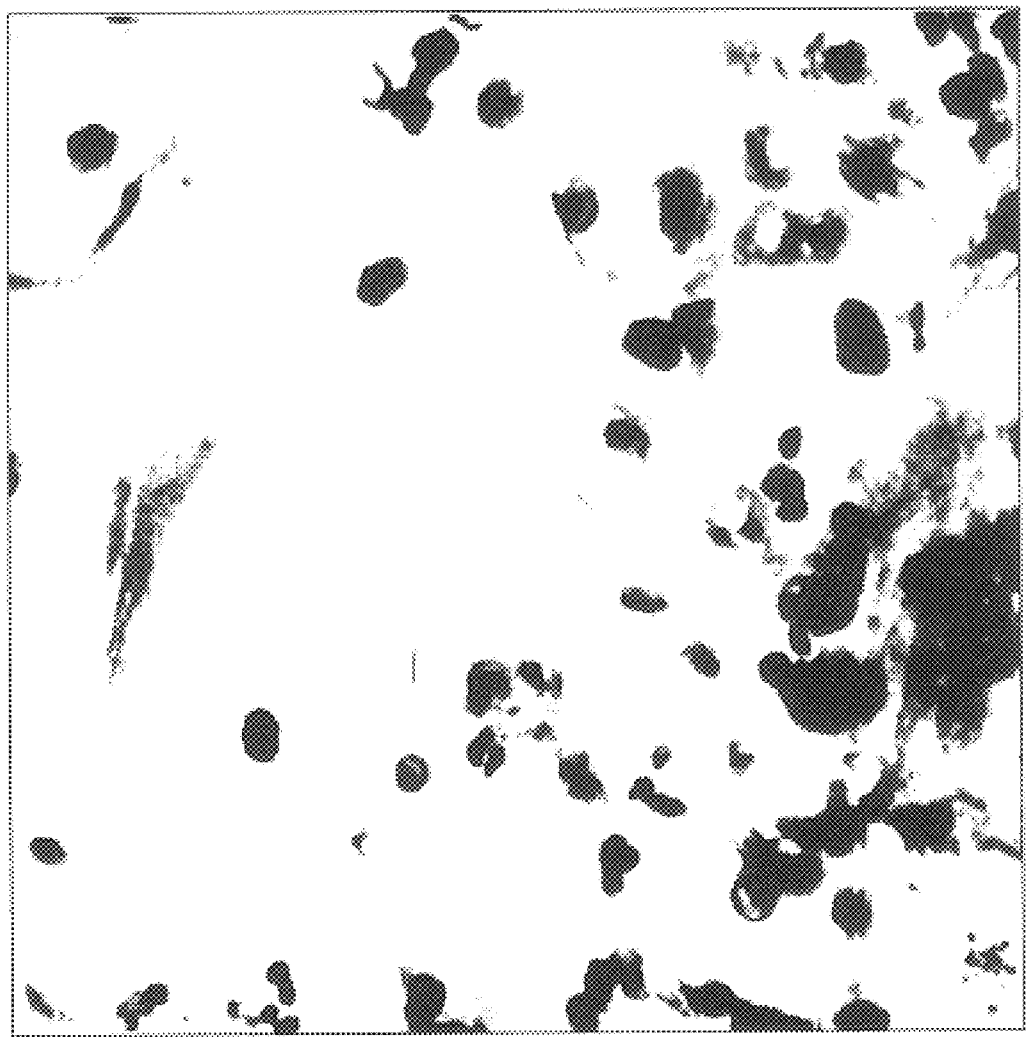
FIG. 13 shows an image of a biological specimen collected using a 555 nm filter minus information from objects stained with a chromogen.

Now refer to FIG. 13, FIG. 13 shows that the accuracy of the dye analysis can be demonstrated by using the extinction coefficient values produced by the analysis to subtract the effects of a dye from a captured image. FIG. 13 shows the image collected at 555 nm with the effects of chromogen 1 removed. Demonstrating that the extinction coefficients from the analysis were accurate.

Figure 14:
FIG. 14 shows an image of a biological specimen collected using a 555 nm filter minus information from objects stained with two chromogens.

Now refer to FIG. 14 which shows the further removal of the second dye leaving very little contrast in the resulting image further demonstrating the accuracy of the extinction coefficient.

TABLE 1

Cross Correlation Table, Ref = 509 nm

| Reference Wavelength | Secondary Wavelength | Structure in Mask | Pixel Count | Average of Epsilon | Standard Dev of Epsilon | Correlation Coefficient |
|---|---|---|---|---|---|---|
| 509 nm | 410 nm | Blue and Green Cytoplasm | 126189 | 0.5979 | 0.3298 | 0.8681 |
| 509 nm | 450 nm | Blue and Green Cytoplasm | 126488 | 0.495 | 0.163 | 0.949 |
| 509 nm | 509 nm | Blue and Green Cytoplasm | 126598 | 1 | 0 | 1 |
| 509 nm | 555 nm | Blue and Green Cytoplasm | 126402 | 0.8064 | 0.2802 | 0.9255 |
| 509 nm | 608 nm | Blue and Green Cytoplasm | 126859 | 1.0901 | 1.1032 | 0.7029 |
| 509 nm | 657 nm | Blue and Green Cytoplasm | 126824 | 1.5148 | 1.8286 | 0.675 |
| 509 nm | 410 nm | Pink and Purple Cytoplasm | 64807 | 0.3117 | 0.0881 | 0.8771 |
| 509 nm | 450 nn | Pink and Purple Cytoplasm | 64808 | 0.3618 | 0.0679 | 0.9419 |
| 509 nm | 509 nm | Pink and Purple Cytoplasm | 64808 | 1 | 0 | 1 |
| 509 nm | 555 nn | Pink and Purple Cytoplasm | 64808 | 0.5942 | 0.0987 | 0.944 |
| 509 nm | 608 nm | Pink and Purple Cytoplasm | 64808 | 0.3235 | 0.1537 | 0.7697 |
| 509 nm | 657 nm | Pink and Purple Cytoplasm | 64808 | 0.3893 | 0.1829 | 0.7694 |
| 509 nm | 410 nm | Nuclei | 20665 | 0.4377 | 0.116 | 0.5865 |
| 509 nm | 450 nm | Nuclei | 20665 | 0.4342 | 0.0653 | 0.8668 |
| 509 nm | 509 nm | Nuclei | 20665 | 1 | 0 | 1 |
| 509 nm | 555 nm | Nuclei | 20665 | 0.8166 | 0.1512 | 0.7667 |
| 509 nm | 608 nm | Nuclei | 20665 | 0.7407 | 0.3062 | 0.1651 |
| 509 nm | 657 nm | Nuclei | 20665 | 0.8425 | 0.3233 | 0.1315 |

TABLE 2

Cross Correlation Table, Ref = 608 nm

| Reference Wavelength | Secondary Wavelength | Structure in Mask | Pixel Count | Average of Epsilon | Standard Dev of Epsilon | Correlation Coefficient |
|---|---|---|---|---|---|---|
| 608 nm | 410 nm | Blue and Green Cytoplasm | 126189 | 0.6296 | 0.3776 | 0.8723 |
| 608 nm | 450 nm | Blue and Green Cytoplasm | 125488 | 0.5508 | 0.3157 | 0.747 |
| 608 nm | 509 nm | Blue and Green Cytoplasm | 126598 | 1.1755 | 0.8235 | 0.7029 |
| 608 nm | 555 nm | Blue and Green Cytoplasm | 126402 | 0.8657 | 0.4024 | 0.8842 |
| 608 nm | 608 nm | Blue and Green Cytoplasm | 126859 | 1 | 0 | 1 |
| 608 nm | 657 nm | Blue and Gneen Cytoplasm | 126824 | 1.3821 | 0.3482 | 0.9882 |
| 608 nm | 410 nm | Pink and Purple Cytoplasm | 64807 | 1.1162 | 0.4588 | 0.9082 |
| 608 nm | 450 nm | Pink and Purple Cytoplasm | 64808 | 1.357 | 0.6712 | 0.8695 |
| 608 nm | 509 nm | Pink and Purple Cytoplasm | 64808 | 3.9804 | 2.4025 | 0.7697 |
| 608 nm | 555 nm | Pink and Purple Cytoplasm | 64808 | 2.2175 | 1.0595 | 0.905 |
| 608 nm | 608 nm | Pink and Purple Cytoplasm | 64808 | 1 | 0 | 1 |
| 608 nm | 657 nm | Pink and Purple Cytoplasm | 64808 | 1.2101 | 0.1498 | 0.9775 |
| 608 nm | 410 nm | Nuclei | 20665 | 0.6408 | 0.1618 | 0.7024 |
| 608 nm | 450 nm | Nuclei | 20665 | 0.6634 | 0.2134 | 0.4847 |
| 608 nm | 509 nm | Nuclei | 20665 | 1.598 | 0.6609 | 1.1651 |
| 608 nm | 555 nm | Nuclei | 20665 | 1.223 | 0.3394 | 0.6689 |
| 608 nm | 608 nm | Nuclei | 20665 | 1 | 0 | 1 |
| 608 nm | 657 nm | Nuclei | 20665 | 1.1592 | 0.1445 | 0.9425 |

Table 1 shows the outcome of the cross-correlation in which the 509 nm image was used as the reference image, and each of the other five wavelengths were tried as secondary wavelengths. Table 2 shows similar data with the 608 nm image serving as the reference.

As can be seen in FIG. 4, contrast in the 555 nm image is provided by strong contributions from both Chromogen 1 and Chromogen 2. The attenuation measurements at the adjacent wavelengths can be used to separate these two components of the attenuation at 555 nm.

The offline extinction coefficient measurement method was used. Segmentation masks were produced by using the 657 nm, 555 nm, and 450 nm images as a red, green, and blue (RGB) triplet. The RGB triplet was converted to a hue, saturation, and value (HSV) triplet using an algorithm well known in the art. The segmentation was accomplished by selecting pixels that fell inside narrow bands of both hue and saturation.

From the pink/purple cytoplasm mask, a good estimate of the ratio of the extinction coefficients for Chromogen 1 at 555 nm and at 509 nm, which is about 0.59 (correlation of 0.944) was obtained. From the blue/green cytoplasm, a ratio of extinction coefficients of Chromogen 2 at 555 nm and at 608 nm of about 0.87 (correlation of 0.88) was obtained.

Other inferences can be gleaned from the correlation data. A further evaluation was performed using the segmentation mask for nuclei shown in FIG. 12. Both Chromogen 1 and Chromogen 2 stain the nuclei strongly, and act independently. However, a surprising rise in the correlation of the 608 nm image to the 450 and 410 nm images is seen for nuclei in Table 2. However, *Conn's Biological Stains, Ninth Edition*, page 472, cites a primary peak for hematoxylin, which is a component of Chromogen 2, at 560 nm and a secondary peak at 430 nm, which explains the high correlation. This observation demonstrates the utility of the cross-correlation method.

Using the extinction coefficient ratios from Tables 1 and 2, the contribution of Chromogen 1 can be removed from the image at 555 nm. The resulting new image is shown in FIG.

13. By way of illustration, we can take the next step of removing the contribution of Chromogen 2 from the new image. Ideally the result would be an empty (all white) image. FIG. 14 shows the actual result.

The determination of extinction coefficients is probably best performed using the offline method on carefully prepared test specimens, repeating the measurements periodically to check the stability of the staining process. If slide staining is very unstable, the option exists to use the online method to perform the extinction coefficient calculation on every slide. In this case, the number of cross-correlations can be restricted to just those cases where high correlation values are expected. That is, knowledge of how the chromogens should behave can reduce the amount of computation. The purpose of the computation would be that of refining the coefficient values to fit a particular specimen.

Figure 15A:
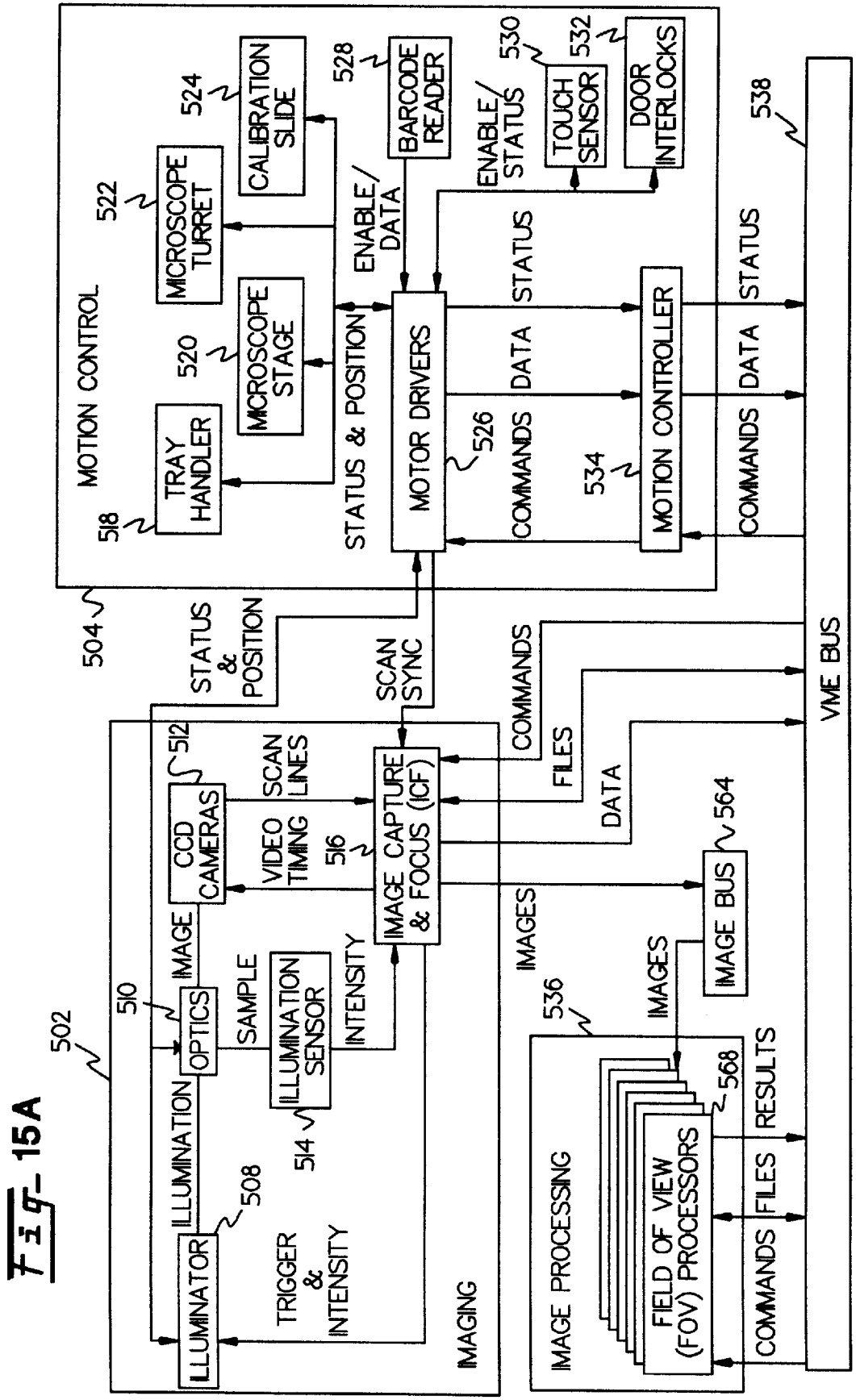
Figure 15B:
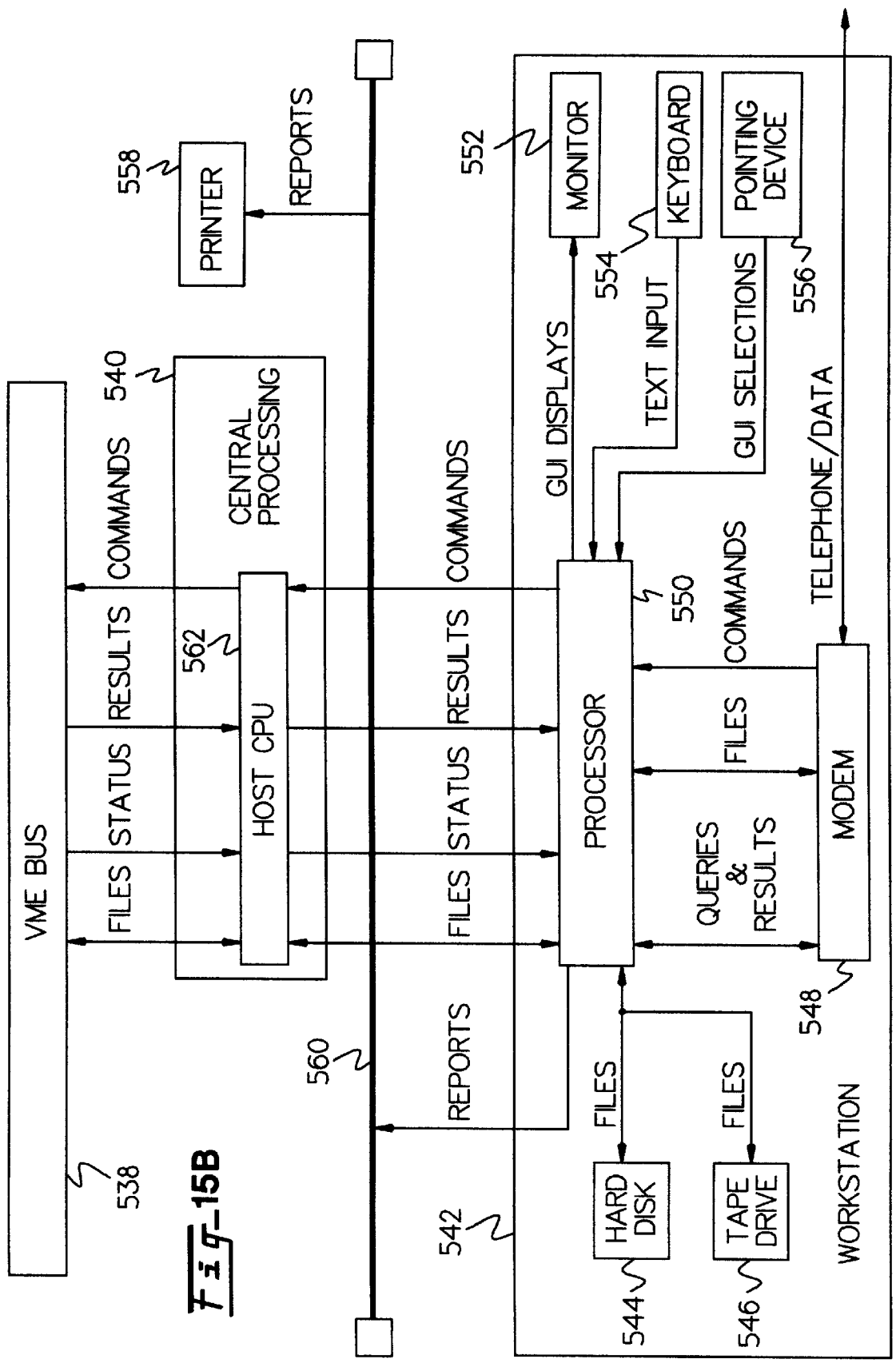

Refer to FIGS. 15A, 15B and 15C that show a schematic diagram of one embodiment of the apparatus of the invention for performing slide classification from multiple wavelength images. While the method and apparatus of the invention will be discussed in terms of an example herein related to an automated cytology apparatus, it will be understood that the invention is not so limited. The features and principles of the invention may be applied to other biological slide preparation types such as sputum slides, blood slides, other pathology slides, etc.

The apparatus of the invention comprises an imaging system 502, a motion control system 504, an image processing system 536, a central processor 540, and a workstation 542. The imaging system 502 is comprised of an illuminator 508, imaging optics 510, a CCD camera 512, an illumination sensor 514 and an image capture and focus system 516. The camera may be a high-resolution camera as is well known in the art. The image capture and focus system 516 provides video timing data to the CCD cameras 512, the CCD cameras 512 provide images comprising scan lines to the image capture and focus system 516. Illumination sensor intensity is provided to the image capture and focus system 516 where an illumination sensor 514 receives the sample of the image from the optics 510. In one embodiment of the invention, the optics may further comprise an automated microscope. The illuminator 508 provides illumination of a slide. The image capture and focus system 516 provides data to a VME bus 538. The VME bus 538 distributes the data to an image processing system 536. The image processing system 536 is comprised of field-of-view processors 568. The images are sent along the image bus 564 from the image capture and focus system 516. The central processor 540 controls the operation of the invention through the VME bus 538. In one embodiment, the central processor 562 comprises a Motorola 68060 CPU. The motion control system 504 is comprised of a tray handler 518, a microscope stage 520, a microscope turret 522, and a calibration slide 524. The motor drivers 526 position the slide under the optics. A bar code reader 528 reads a barcode located on the slide 524. A touch sensor 530 determines whether a slide is under the microscope objectives, and door interlock 532 prevents operation in case the doors are open. Motion controller 534 controls the motor drivers 526 in response to the central processor 540. An ETHERNET communication system 560 communicates to a workstation 542 to provide control of the system. Workstation processor 550 controls a hard disk 544. In one embodiment, workstation 542 may comprise a SUN SPARC ULTRA workstation. A tape drive 546 is connected to the workstation processor 550 as well as a modem 548, a monitor 552, a keyboard 554, and a mouse-pointing device 556. A printer 558 is connected to the ETHERNET network system 560.

During image collection integrity checking, the central processor 540, running a real time operating system, controls the automated microscope and the processor to acquire and digitize images from the microscope. The flatness of the slide may be checked, for example, by contacting the four corners of the slide using a computer controlled touch sensor. The central processor 540 also controls the microscope stage to position the specimen under the microscope objective, and from one to 15 field of view (FOV) processors 568 which receive images under control of the central processor 540.

Referring now to FIG. 15C, there is shown placement of a slide 12 into an optical path of an automated microscope 511 having a turret 522 and a CCD camera 512. The slide 12 may be mounted on a stage 520 substantially in a horizontal X,Y plane that intersects the optical path. The stage 520 is movable in the X, Y plane as well as along a Z axis which is perpendicular to the X, Y plane and which is parallel to the optical axis of the optics 510 of the automated microscope 511. The turret 522 may comprise multiple objective lenses as is well known in the art. The microscope turret control 523 provides signals in a well-known manner for positioning a selected objective lens into position for viewing the slide 12. Illuminator 508 illuminates the slide 12.

It is to be understood that the various processes described herein may be implemented in software suitable for running on a digital processor. The software may be embedded, for example, in the central processor 540.

The slide 12 may be coverslipped. The coverslip may be detected following the methods described in assignee's United States Patents and copending United States Patent applications referred to herein.

The automated analysis system may be operated in two modes: quality control mode and screening mode. In the quality control mode, the automated analysis system generates a quality control score. In the screening mode, the automated analysis system generates an analysis score. These automated methods of performing screening and quality control steps employ software used by the central processor 540 to provide an analysis score or quality control score. The software operates on data that is a machine representation of a slide. The software employs thresholds that are used to determine the likelihood of normalcy or malignancy of the slide. The thresholds may also be used to determine subpopulations of slides for quality control checking or to select subpopulations of slides that are so clearly normal that they do not need checking.

The following United States Patents and Patent Applications are incorporated by reference hereto:

U.S. Pat. No. 5,315,700, issued May 24, 1994 to Johnston et al., entitled METHOD AND APPARATUS FOR RAPIDLY PROCESSING DATA SEQUENCES;

U.S. Pat. No. 5,361,140, issued Nov. 1, 1994, to Hayenga et al., entitled METHOD AND APPARATUS FOR DYNAMIC CORRECTION OF MICROSCOPIC IMAGE SIGNALS;

U.S. Pat. No. 5,699,794, issued Dec. 23, 1997, to Fleck, entitled APPARATUS FOR AUTOMATED URINE SEDIMENT SAMPLE HANDLING;

U.S. Pat. No. 5,528,703, issued Jun. 18, 1996, to Lee, entitled FWC: METHOD FOR IDENTIFYING OBJECTS USING DATA PROCESSING TECHNIQUES, which is a file wrapper continuation of abandoned U.S. patent application Ser. No. 07/838,395, filed Feb. 18, 1992;

pending U.S. patent application Ser. No. 08/485,182, filed Jun. 7, 1995, to Lee et al., entitled INTERACTIVE

METHOD AND APPARATUS FOR SORTING BIOLOGICAL SPECIMENS;

U.S. Pat. No. 5,647,025, issued Jul. 8, 1997, to Frost et al., entitled AUTOMATIC FOCUSING OF BIOMEDICAL SPECIMENS APPARATUS;

U.S. Pat. No. 5,912,699, issued Jun. 15, 1999 to Hayenga et al., entitled CIP: METHOD AND APPARATUS FOR RAPID CAPTURE OF FOCUSED MICROSCOPIC IMAGES, which is a continuation-in-part of abandoned U.S. patent application Ser. No. 07/838,063, filed Feb. 18, 1992;

U.S. Pat. No. 5,715,326, issued Feb. 3, 1998, to Ortyn et al., entitled CYTOLOGICAL SYSTEM ILLUMINATION INTEGRITY CHECKING APPARATUS AND METHOD;

U.S. Pat. No. 5,581,631, issued Dec. 3, 1996, to Ortyn et al., entitled CYTOLOGICAL SYSTEM IMAGE COLLECTION INTEGRITY CHECKING APPARATUS;

U.S. Pat. No. 5,557,097, issued Sep. 17, 1996, to Ortyn et al., entitled CYTOLOGICAL SYSTEM AUTOFOCUS INTEGRITY CHECKING APPARATUS;

U.S. Pat. No. 5,499,097, issued Mar. 12, 1996, to Ortyn et al., entitled METHOD AND APPARATUS FOR CHECKING AUTOMATED OPTICAL SYSTEM PERFORMANCE REPEATABILITY;

U.S. Pat. No. 5,757,954, issued May 26, 1998, to Kuan et al., entitled FIELD PRIORITIZATION APPARATUS AND METHOD;

U.S. Pat. No. 5,627,908, issued May 6, 1997, to Lee et al., entitled METHOD FOR CYTOLOGICAL SYSTEM DYNAMIC NORMALIZATION;

U.S. Pat. No. 5,638,459, issued Jun. 10, 1997, to Rosenlof et al., entitled METHOD AND APPARATUS FOR DETECTING A MICROSCOPE SLIDE COVERSLIP;

U.S. Pat. No. 5,566,249, issued Oct. 15, 1996, to Rosenlof et al., entitled APPARATUS FOR DETECTING BUBBLES IN COVERSLIP ADHESIVE;

allowed U.S. patent application Ser. No. 08/309,250, filed Sep. 20, 1994, for which the issue fee has been paid, to Lee et al., entitled APPARATUS FOR THE IDENTIFICATION OF FREE-LYING CELLS;

U.S. Pat. No. 5,740,269, issued Apr. 14, 1998, to Oh et al., entitled A METHOD AND APPARATUS FOR ROBUST BIOLOGICAL SPECIMEN CLASSIFICATION;

U.S. Pat. No. 5,715,327, issued Feb. 3, 1998, to Wilhelm et al., entitled METHOD AND APPARATUS FOR DETECTION OF UNSUITABLE CONDITIONS FOR AUTOMATED CYTOLOGY SCORING;

U.S. Pat. No. 5,692,066, issued Nov. 25, 1997, to Lee et al., entitled METHOD AND APPARATUS FOR IMAGE PLANE MODULATION PATTERN RECOGNITION;

U.S. Pat. No. 5,671,288, issued Sep. 23, 1997, to Wilhelm et al., entitled METHOD AND APPARATUS FOR ASSESSING SLIDE AND SPECIMEN PREPARATION QUALITY;

U.S. Pat. No. 5,619,428, issued Apr. 8, 1997, to Lee et al., entitled METHOD AND APPARATUS FOR INTEGRATING AN AUTOMATED SYSTEM TO A LABORATORY;

U.S. Pat. No. 5,621,519, issued Apr. 15, 1997, to Frost et al., entitled IMAGING SYSTEM TRANSFER FUNCTION CONTROL METHOD AND APPARATUS;

U.S. Pat. No. 5,642,441, issued Jun. 24, 1997, to Riley et al., entitled APPARATUS AND METHOD FOR MEASURING FOCAL PLANE SEPARATION;

U.S. Pat. No. 5,787,208, issued Jul. 28, 1998, to Oh et al., entitled IMAGE ENHANCEMENT METHOD AND APPARATUS;

pending U.S. patent application Ser. No. 08/924,351, filed Sep. 5, 1997, to Kuan et al., entitled DYNAMIC CONTROL AND DECISION MAKING METHOD AND APPARATUS;

U.S. Pat. No. 5,625,706, issued Apr. 29, 1997, to Lee et al., entitled METHOD AND APPARATUS FOR CONTINUOUSLY MONITORING AND FORECASTING SLIDE AND SPECIMEN PREPARATION FOR A BIOLOGICAL SPECIMEN POPULATION;

U.S. Pat. No. 5,745,601, issued Apr. 28, 1998, to Lee et al., entitled ROBUSTNESS OF CLASSIFICATION MEASUREMENT APPARATUS AND METHOD;

U.S. Pat. No. 5,781,667, issued Jul. 14, 1998, to Schmidt et al., entitled APPARATUS FOR HIGH SPEED MORPHOLOGICAL PROCESSING;

U.S. Pat. No. 5,642,43 3, issued Jun. 24, 1997, to Lee et al., entitled METHOD AND APPARATUS FOR IMAGE CONTRAST QUALITY EVALUATION;

U.S. Pat. No. 5,797,130, issued Aug. 18, 1998, to Nelson et al., entitled FWC: METHOD FOR TESTING PROFICIENCY IN SCREENING IMAGES OF BIOLOGICAL SLIDES, which is a file wrapper continuation of abandoned U.S. patent application Ser. No. 08/153,293, filed Nov. 16, 1993;

U.S. Pat. No. 5,787,188, issued Jul. 28, 1998, to Nelson et al., entitled FWC: METHOD FOR IDENTIFYING NORMAL BIOMEDICAL SPECIMENS, which is a file wrapper continuation of abandoned U.S. patent application Ser. No. 07/838,064, filed Feb. 18, 1992, to Nelson et al.;

U.S. Pat. No. 5,710,842, issued Jan. 20, 1998, to Lee entitled DIV: METHOD FOR IDENTIFYING OBJECTS USING DATA PROCESSING TECHNIQUES, which is a divisional of U.S. Pat. No. 5,528,703, ibid., which is a file wrapper continuation of abandoned U.S. patent application Ser. No. 07/838,395, filed Feb. 18, 1992;

allowed U.S. patent application Ser. No. 08/788,239, for which the issue fee has been paid, filed Jan. 25, 1997, to Oh et al., entitled METHOD AND APPARATUS FOR ALIAS FREE MEASUREMENT OF OPTICAL TRANSFER FUNCTION;

U.S. Pat. No. 5,677,762, issued Oct. 14, 1997, to Ortyn et al., entitled FWC: APPARATUS FOR ILLUMINATION STABILIZATION AND HOMOGENIZATION, which is a file wrapper continuation of abandoned U.S. patent application Ser. No. 08/309,064, filed Sep. 20, 1994;

U.S. Pat. No. 5,787,189, issued Jul. 28, 1998, to Lee et al., entitled FWC: BIOLOGICAL ANALYSIS SYSTEM SELF CALIBRATION APPARATUS, which is a file wrapper continuation of abandoned U.S. patent application Ser. No. 08/309,115, filed Sep. 20, 1994;

U.S. Pat. No. 5,654,535, issued Aug. 5, 1997, to Ortyn et al., entitled DIV: CYTOLOGICAL SYSTEM AUTOFOCUS INTEGRITY CHECKING APPARATUS, which is a divisional of U.S. Pat. No. 5,557,097, ibid.;

U.S. Pat. No. 5,828,776, issued Oct. 27, 1998, to Lee et al., entitled FWC: APPARATUS FOR IDENTIFICA- TION AND INTEGRATION OF MULTIPLE CELL PATTERNS, which is a file wrapper continuation of abandoned U.S. patent application Ser. No. 08/308,992, filed Sep. 20, 1994, to Lee et al.;

pending U.S. patent application Ser. No. 09/121,012, filed Jul. 22, 1998, to Lee et al., entitled DIV: APPARATUS FOR THE IDENTIFICATION OF FREE-LYING CELLS, which is a divisional of allowed U.S. patent application Ser. No. 08/309,250, ibid.;

pending U.S. patent application Ser. No. 09/120,860, filed Jul. 22, 1998, to Lee et al., entitled DIV: APPARATUS FOR THE IDENTIFICATION OF FREE-LYING CELLS, which is a divisional of allowed U.S. patent application Ser. No. 08/309,250, ibid.;

pending U.S. patent application Ser. No. 09/120,612, filed Jul. 22, 1998, to Lee et al., entitled DIV: APPARATUS FOR THE IDENTIFICATION OF FREE-LYING CELLS, which is a divisional of allowed U.S. patent application Ser. No. 08/309,250, ibid.;

U.S. Pat. No. 5,875,258, issued Feb. 23, 1999, to Ortyn et al., entitled FWC: BIOLOGICAL SPECIMEN ANALYSIS SYSTEM PROCESSING INTEGRITY CHECKING APPARATUS, which is a file wrapper continuation of abandoned U.S. patent application Ser. No. 08/309,249, filed Sep. 20, 1994;

U.S. Pat. No. 5,812,692, issued Sep. 22, 1998, to Rosenlof et al., entitled DIV: METHOD AND APPARATUS FOR DETECTING A MICROSCOPE SLIDE COVERSLIP, which is a divisional of U.S. Pat. No. 5,638,459, ibid.;

pending U.S. patent application Ser. No. 08/767,457, filed Dec. 16, 1996, to Lee et al., entitled METHOD AND APPARATUS FOR EFFICACY IMPROVEMENT IN MANAGEMENT OF CASES WITH EQUIVOCAL SCREENING RESULTS;

pending U.S. patent application Ser. No. 08/877,368, filed Jun. 17, 1997, to Lee et al., entitled DIV: METHOD AND APPARATUS FOR IMAGE PLANE MODULATION PATTERN RECOGNITION, which is a divisional of U.S. Pat. No. 5,692,066, ibid.;

U.S. Pat. No. 5,892,218, issued Apr. 4, 1999, to Ortyn et al., entitled DIV: CYTOLOGICAL SYSTEM AUTOFOCUS INTEGRITY CHECKING APPARATUS, which is a divisional of U.S. Pat. No. 5,654,535, ibid., which is a divisional of U.S. Pat. No. 5,557,097, ibid.;

U.S. Pat. No. 5,760,387, issued Jun. 2, 1998, to Ortyn et al., entitled DIV: CYTOLOGICAL SYSTEM AUTOFOCUS INTEGRITY CHECKING APPARATUS, which is a divisional of U.S. Pat. No. 5,654,535, ibid., which is a divisional of U.S. Pat. No. 5,557,097, ibid.;

U.S. Pat. No. 5,841,124, issued Nov. 24, 1998, to Ortyn et al., entitled DIV: CYTOLOGICAL SYSTEM AUTOFOCUS INTEGRITY CHECKING APPARATUS, which is a divisional of U.S. Pat. No. 5,654,535, ibid., which is a divisional of U.S. Pat. No. 5,557,097, ibid.;

U.S. Pat. No. 5,763,871, issued Jun. 9, 1998, to Ortyn et al., entitled DIV: CYTOLOGICAL SYSTEM AUTOFOCUS INTEGRITY CHECKING APPARATUS, which is a divisional of U.S. Pat. No. 5,654,535, ibid., which is a divisional of U.S. Pat. No. 5,557,097, ibid.;

U.S. Pat. No. 5,877,489, issued Mar. 2, 1999, to Ortyn et al., entitled DIV: CYTOLOGICAL SYSTEM AUTOFOCUS INTEGRITY CHECKING APPARATUS, which is a divisional of U.S. Pat. No. 5,654,535, ibid., which is a divisional of U.S. Pat. No. 5,557,097, ibid.;

U.S. Pat. No. 5,883,982, issued Mar. 16, 1999, to Riley et al., entitled DIV: ASTIGMATISM MEASUREMENT APPARATUS AND METHOD BASED ON A FOCAL PLANE SEPARATION, which is a divisional of U.S. Pat. No. 5,642,441, ibid.;

allowed U.S. patent application Ser. No. 08/900,341, filed Jul. 25, 1997, for which the issue fee has been paid, to Riley et al., entitled MODULATION TRANSFER FUNCTION TEST COMPENSATION FOR TEST PATTERN DUTY CYCLE;

pending U.S. patent application Ser. No. 08/888,115, filed Jul. 3, 1997, to Lee et al., entitled METHOD AND APPARATUS FOR MASKLESS SEMICONDUCTOR AND LIQUID CRYSTAL DISPLAY INSPECTION;

pending U.S. patent application Ser. No. 08/888,120, filed Jul. 3, 1997, to Lee et al., entitled METHOD AND APPARATUS FOR A REDUCED INSTRUCTION SET ARCHITECTURE FOR MULTIDIMENSIONAL IMAGE PROCESSING;

pending U.S. patent application Ser. No. 08/888,119, filed Jul. 3, 1997, to Lee et al., entitled METHOD AND APPARATUS FOR INCREMENTAL CONCURRENT LEARNING IN AUTOMATIC SEMICONDUCTOR WAFER AND LIQUID CRYSTAL DISPLAY DEFECT CLASSIFICATION;

pending U.S. patent application Ser. No. 08/888,116, filed Jul. 3, 1997, to Lee et al., entitled METHOD AND APPARATUS FOR SEMICONDUCTOR WAFER AND LCD INSPECTION USING MULTIDIMENSIONAL IMAGE DECOMPOSITION AND SYNTHESIS;

pending U.S. patent application Ser. No. 09/006,457, filed Jan. 13, 1998, to Kuan et al., entitled A METHOD AND APPARATUS FOR OPTIMIZING BIOLOGICAL AND CYTOLOGICAL SPECIMEN SCREENING AND DIAGNOSIS;

allowed U.S. patent application Ser. No. 08/867,017, filed Jun. 3, 1997, for which the issue fee has been paid, to Lee et al., entitled FWC: CYTOLOGICAL SLIDE SCORING APPARATUS, which is a file wrapper continuation of abandoned U.S. patent application Ser. No. 08/309,931, filed Sep. 20, 1994;

U.S. Pat. No. 5,587,833, issued Dec. 24, 1996, to Kamentsky entitled COMPUTERIZED MICROSCOPE SPECIMEN ENCODER;

U.S. Pat. No. 5,602,674, issued Feb. 11, 1997, to Weissman et al., entitled COMPUTERIZED SPECIMEN ENCODER;

U.S. Pat. No. 5,561,556, issued Oct. 1, 1996, to Weissman entitled SLIDE ANALYSIS SYSTEM WITH SLIDE HAVING SELF CONTAINED MICROSCOPE ANALYSIS INFORMATION;

U.S. Pat. No. 5,793,969, issued Aug. 11, 1998, to Kamentsky et al., entitled NETWORK REVIEW AND ANALYSIS OF COMPUTER ENCODER SLIDES;

U.S. Pat. No. 5,790,308, issued Aug. 4, 1998, to Kamentsky entitled COMPUTERIZED MICROSCOPE SPECIMEN ENCODER;

U.S. Pat. No. 5,694,212, issued Dec. 2, 1997, to Weissman, entitled METHOD FOR CALIBRATING SPECIMEN WITH SPECIMEN HOLDER OF A MICROSCOPE;

U.S. Pat. No. 5,581,487, issued Dec. 3, 1996, to Kelly entitled METHOD AND APPARATUS FOR MICROSCOPIC SCREENING OF CYTOLOGICAL SAMPLES;

U.S. Pat. No. 5,867,610, issued Feb. 2, 1999, to Lee entitled DIV: METHOD FOR IDENTIFYING OBJECTS USING DATA PROCESSING TECHNIQUES, which is a divisional of U.S. Pat. No. 5,710,842, ibid.;

U.S. Pat. No. 5,799,101, issued Aug. 25, 1998, to Lee et al., entitled FWC: METHOD AND APPARATUS FOR HIGHLY EFFICIENT COMPUTER AIDED SCREENING, which is a file wrapper continuation of abandoned U.S. patent application Ser. No. 08/315,719, filed Sep. 30, 1994;

pending U.S. patent application Ser. No. 08/912,061, filed Aug. 15, 1997, to Ortyn et al., entitled DIV: CYTOLOGICAL SYSTEM ILLUMINATION INTEGRITY CHECKING APPARATUS AND METHOD, which is a divisional of U.S. Pat. No. 5,715,326, ibid.;

pending U.S. patent application Ser. No. 08/911,807, filed Aug. 15, 1997, to Ortyn et al., entitled DIV: CYTOLOGICAL SYSTEM ILLUMINATION INTEGRITY CHECKING APPARATUS AND METHOD, which is a divisional of U.S. Pat. No. 5,715,326, ibid.;

pending U.S. patent application Ser. No. 08/911,612, filed Aug. 15, 1997, to Ortyn et al., entitled DIV: CYTOLOGICAL SYSTEM ILLUMINATION INTEGRITY CHECKING APPARATUS AND METHOD, which is a divisional of U.S. Pat. No. 5,715,326, ibid.;

pending U.S. patent application Ser. No. 08/912,115, filed Aug. 15, 1997, to Ortyn et al., entitled DIV: CYTOLOGICAL SYSTEM ILLUMINATION INTEGRITY CHECKING APPARATUS AND METHOD, which is a divisional of U.S. Pat. No. 5,715,326, ibid.;

pending U.S. patent application Ser. No. 08/911,644, filed Aug. 15, 1997, to Ortyn et al., entitled DIV: CYTOLOGICAL SYSTEM ILLUMINATION INTEGRITY CHECKING APPARATUS AND METHOD, which is a divisional of U.S. Pat. No. 5,715,326, ibid.;

pending U.S. patent application Ser. No. 08/911,611, filed Aug. 15, 1997, to Ortyn et al., entitled DIV: CYTOLOGICAL SYSTEM ILLUMINATION INTEGRITY CHECKING APPARATUS AND METHOD, which is a divisional of U.S. Pat. No. 5,715,326, ibid.;

allowed U.S. patent application Ser. No. 08/969,970, filed Nov. 13, 1997, to Meyer et al., entitled FWC: APPARATUS FOR AUTOMATED IDENTIFICATION OF THICK CELL GROUPINGS ON A BIOLOGICAL SPECIMEN, which is a file wrapper continuation of abandoned U.S. patent application Ser. No. 08/309,116, filed Sep. 20, 1994;

allowed U.S. patent application Ser. No. 08/927,379, filed Sep. 12, 1997, to Wilhelm et al., entitled FWC: APPARATUS FOR AUTOMATED IDENTIFICATION OF CELL GROUPINGS ON A BIOLOGICAL SPECIMEN, which is a file wrapper continuation of abandoned U.S. patent application Ser. No. 08/309,061, filed Sep. 20, 1994;

pending U.S. patent application Ser. No. 08/970,904, filed Nov. 14, 1997, to Weissman et al., entitled FWC: FOLDING SLIDE HOLDER, which is a file wrapper continuation of abandoned U.S. patent application Ser. No. 08/582,495, filed Jan. 3, 1996;

pending U.S. patent application Ser. No. 09/014,984, filed Jan. 28, 1998, to Ellison et al., entitled METHOD AND APPARATUS FOR RANKED REVIEW OF BIOLOGICAL SPECIMENS;

U.S. Pat. No. 5,862,265, issued Jan. 19, 1999, to Riley et al., entitled DIV: ASTIGMATISM MEASUREMENT APPARATUS AND METHOD, which is a divisional of U.S. Pat. No. 5,883,982, ibid., which is a divisional of U.S. Pat. No. 5,642,441, ibid.;

pending U.S. patent application Ser. No. 09/082,580, filed May 21, 1998, to Kuan et al., entitled DIV: FIELD PRIORITIZATION APPARATUS AND METHOD, which is a divisional of U.S. Pat. No. 5,757,954, ibid.;

pending U.S. patent application Ser. No. 09/291,531, filed Apr. 14, 1999 to Boisseranc et al., entitled METHOD AND APPARATUS FOR DETERMINING MICROSCOPE SPECIMEN PREPARATION TYPE;

pending U.S. patent application Ser. No. 09/291,519, filed Apr. 14, 1999 to Boisseranc et al., entitled METHOD AND APPARATUS FOR DETERMINING MICROSCOPE SPECIMEN PREPARATION TYPE;

A Continued Prosecution Application entitled CPA: METHOD AND APPARATUS FOR DETECTION OF UNSUITABLE CONDITIONS FOR AUTOMATED CYTOLOGY SCORING of prior U.S. patent application Ser. No. 08/914,292, filed Aug. 18, 1997, to Wilhelm et al., which is a divisional of U.S. Pat. No. 5,715,327, ibid.;

a Continued Prosecution Application entitled CPA: APPARATUS FOR AUTOMATED IDENTIFICATION OF THICK CELL GROUPINGS ON A BIOLOGICAL SPECIMEN of prior U.S. patent application Ser. No. 08/969,970, ibid., which is a file wrapper continuation of abandoned U.S. patent application Ser. No. 08/309,116, ibid.;

a Continued Prosecution Application entitled CPA: CYTOLOGICAL SYSTEM ILLUMINATION INTEGRITY CHECKING APPARATUS AND METHOD of prior U.S. patent application Serial No. 08/911,611, ibid, which is a divisional of U.S. Pat. No. 5,715,326, ibid.; and a Continued Prosecution Application entitled CPA: CYTOLOGICAL SYSTEM ILLUMINATION INTEGRITY CHECKING APPARATUS AND METHOD of prior U.S. patent application Serial No. 08/911,612, ibid, which is a divisional of U.S. Pat. No. 5,715,326, ibid.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for separating contrasts for images of a biological specimen wherein the biological specimen has been prepared with a chromogen comprising the steps of:

(a) obtaining an image of the biological specimen at a wavelength of interest wherein the image comprises a plurality of pixels;

(b) measuring the zero attenuation grayscale value from clear areas of the image, wherein the zero attenuation grayscale value is $G_N(0)$ and the attenuation coefficient $\alpha_n(i,j)$ is:

$$\alpha_n(i, j) = -\ln\left(\frac{G_n(i, j)}{G_n(0)}\right)$$

where
n=index identifying filter with center wavelength $\lambda_n$;
$G_n(i,j)$=grayscale value for pixel i,j in image collected at $\lambda_n$;
$G_n(0)$=grayscale value for zero attenuation in specimen using filter n; and
$\alpha_n(i,j)$=attenuation coefficient for pixel i,j;

(c) computing the attenuation coefficient for all pixels in the image from the zero attenuation grayscale value and pixel values;

(d) expressing the attenuation coefficient as the concentration times an extinction coefficient for the chromogen at the wavelength of interest; and (e) solving for the concentration of the chromogen at each pixel by dividing the attenuation by the extinction coefficient.

2. The method of claim 1 wherein the attenuation coefficient is:

$$\alpha(i,j) = \epsilon \cdot C$$

where:
$\epsilon$=the extinction coefficient for the chromogen; and
C=the concentration of the chromogen.

3. A method for separating contrast in an image of a biological specimen wherein the biological specimen has been prepared with multiple chromogens comprising the steps of:

(a) obtaining multiple images of the biological specimen wherein each image is taken at a wavelength of interest wherein each image comprises a plurality of pixels;

(b) measuring a zero attenuation grayscale value for each image in clear areas, wherein the zero attenuation grayscale value is $G_n(0)$ and the attenuation coefficient $\alpha_n(i,j)$ is $$\alpha_n(i, j) = -\ln\left(\frac{G_n(i, j)}{G_n(0)}\right) \quad (1.1)$$

where
n=index identifying filter with center wavelength $\lambda n$;
$G_n(i,j)$=grayscale value for pixel i,j in image collected at $\lambda_n$;
$G_n(0)$=grayscale value for zero attenuation in specimen using filter n; and
$\alpha_n(i,j)$=attenuation coefficient for pixel i,j;

(c) computing attenuation coefficients for all pixels in each image from the zero attenuation grayscale value and pixel value; and (d) computing the concentration of each chromogen at a pixel location based on the attenuation coefficients and extinction coefficients at each wavelength of interest.

4. The method of claim 3 further comprising the steps of (a) expressing the attenuation coefficients as the sum of the products of the extinction coefficients at each wavelength of interest times the concentration for each chromogen; and (b) computing the concentration of each chromogen at a pixel location by a series of matrix inversions.

5. The method of claim 3 wherein the attenuation coefficients are expressed as:

$$\alpha_1(i,j) = \epsilon_{1,1} \cdot C_1(i,j) + \epsilon_{2,1} \cdot C_2(i,j) + \ldots + \epsilon_{m,1} \cdot C_m(i,j)$$

$$\alpha_2(i,j) = \epsilon_{1,2} \cdot C_1(i,j) + \epsilon_{2,2} \cdot C_2(i,j) + \ldots + \epsilon_{m,2} \cdot C_m(i,j)$$

$$\alpha_n(i,j) = \epsilon_{1,n} \cdot C_1(i,j) + \epsilon_{2,n} \cdot C_2(i,j) + \ldots + \epsilon_{m,n} \cdot C_m(i,j)$$

where:
(i,j) are the pixel coordinates;
$\alpha_n(i,j)$=attenuation at wavelength "n" for the pixel (i,j);
$\epsilon_{m,n}$=relative extinction coefficient for chromogen "m" at wavelength "n"; and
$C_m(i,j)$=relative concentration of chromogen "m" for pixel (i,j).

6. The method of claim 3 wherein the concentration is:

$$C_1(i,j) = k_{1,1} \cdot \alpha_1(i,j) + k_{1,2} \cdot \alpha_2(i,j) + \ldots + k_{1,n} \cdot \alpha_1(i,j) \quad (10)$$

$$C_2(i,j) = k_{2,1} \cdot \alpha_1(i,j) + k_{2,2} \cdot \alpha_2(i,j) + \ldots + k_{2,n} \cdot \alpha_1(i,j)$$

$$C_m(i,j) = k_{m,1} \cdot \alpha_1(i,j) + k_{m,2} \cdot \alpha_2(i,j) + \ldots + k_{m,n} \cdot \alpha_1(i,j)$$

where:
(i,j) are the pixel coordinates;
$\alpha_n(i,j)$=attenuation at wavelength "n" for the pixel (i,j);
$k_{m,n}$=coefficients from matrix inversions; and
$C_m(i,j)$=relative concentration of chromogen "m" for pixel (i,j).

7. The method of claim 3 further comprising the step of creating a new image $\alpha(i,j)$ according to:

$$\alpha'_1(i,j) = \alpha_1(i,j) - \epsilon_{2,1} \cdot C_2(i,j) - \epsilon_{3,1} \cdot C_3(i,j)$$

$$G(i,j) = N(0) \cdot \epsilon^{-\alpha'1(i,j)}$$

where:
G(i,j)=gray level of pixel (i,j) in new image;
N(0)=gray level for the hypothetical clear area; and
$\alpha'_1(i,j)$=computed attenuation after other chromogens removed.

8. The method of claim 3 further comprising the step of creating a new image $\alpha'(i,j)$ according to equation:

$$\alpha''_1(i,j) = \epsilon_{1,1} \cdot C_1(i,j) + \epsilon''_{2,1} \cdot C_2(i,j) + \epsilon_{3,1} \cdot C_3(i,j)$$

$$G(i,j) = N(0) \cdot \epsilon^{-\alpha''1(i,j)}$$

where:
G(i,j)=gray level of pixel (i,j) in new image;
N(0)=gray level for the hypothetical clear area; and
$\alpha''_1(i,j)$=attenuation for hypothetical chromogen.

9. A method of computing extinction coefficients from a specimen containing a single chromogen comprising the steps of:

(f) selecting a field of view of an image of the specimen at a wavelength of interest;

(g) finding the zero attenuation gray level for the wavelength of interest;

(h) segmenting the field of view into structures using morphological infrastructures of interest;

(i) converting the grayscale value into attenuation values;

(j) selecting an image of maximum attenuation as a reference image; and (k) computing an extinction coefficient for the image, wherein the extinction coefficient is computed by:

$$\varepsilon_{sec} = \frac{E[A_{sec}]}{E[A_{ref}]}$$

where:

$A_{sec}$=attenuation in secondary image, a random variable;

$A_{ref}$=attenuation in the reference image, a random variable; and

E=expectation operator, returns the average of random variable X.

10. The method of claim 9 wherein the extinction coefficient is computed as an average over multiple fields of view.

11. A method of computing relative extinction coefficients from a specimen containing multiple chromogens comprising the steps of:

(a) imaging the specimen to collect multiple images of the specimen, wherein each image is collected at a wavelength of interest;

(c) finding the zero attenuation gray level for each image;

(d) converting the grayscale level into attenuation values;

(f) selecting an image with maximum attenuation as a reference image for each chromogen; and (g) computing a relative extinction coefficient for each chromogen, wherein the extinction coefficient is computing according to the following equation:

$$\varepsilon_{f,m,n} = \frac{E[A_{sec}]}{E[A_{ref}]}$$

where:

$A_{sec}$=attenuation in secondary image, a random variable;

$A_{ref}$=attenuation in the reference image, a random variable;

f=index for the field of view;

m=index for the chromogen; and n=index for the secondary wavelength.

12. The method of claim 11 wherein the relative extinction coefficient is computed as an average over multiple fields of view.

13. The method of claim 11 wherein an image further comprises pixels and wherein the step of calculating the relative extinction coefficient comprises the steps of:

(a) setting an attenuation window for mask generation by comparing the reference image to another image;

(b) generating a segmentation mask comprising all pixels that are in the attenuation window;

(c) computing a correlation coefficient of the elements in the image corresponding to the segmentation mask;

(d) determining whether the correlation coefficient is greater than a predetermined limit and if it is not adjusting the attenuation window and returning to step (b) to generate another segmentation mask and if the correlation coefficient is greater than the predetermined limit then calculating an extinction coefficient for this image.

14. The method of claim 11 wherein the extinction coefficients are computed for all images.

15. The method of claim 14 wherein the correlation coefficient is computed according to $$p(A_1, A_2) = \frac{Cov[A_1, A_2]}{\sqrt{Var(A_1) \cdot Var(A_2)}}$$

where:

$Cov[A_1,A_2]=E[A_1 \cdot A_2]-E[A_1] \cdot E[A_2]$ $Var[A_1]=E[A_1^2]-(E[A_1])^2$ $Var[A_2]=E[A_2^2]=(E[A_2])^2$ $A_n$=attenuation at wavelength n, a random variable.

* * * * *